(12) United States Patent
Wu

(10) Patent No.: US 9,257,269 B2
(45) Date of Patent: Feb. 9, 2016

(54) METHODS AND APPARATUS FOR THE ION MOBILITY BASED SEPARATION AND COLLECTION OF MOLECULES

(71) Applicant: Ching Wu, Acton, MA (US)

(72) Inventor: Ching Wu, Acton, MA (US)

(73) Assignee: Excellims Corporation, Acton, MA (US)

(*) Notice: Subject to any disclaimer, the term of this patent is extended or adjusted under 35 U.S.C. 154(b) by 0 days.

(21) Appl. No.: 13/651,837

(22) Filed: Oct. 15, 2012

(65) Prior Publication Data

US 2013/0037710 A1 Feb. 14, 2013

Related U.S. Application Data

(62) Division of application No. 11/776,392, filed on Jul. 11, 2007, now abandoned.

(60) Provisional application No. 60/807,031, filed on Jul. 11, 2006, provisional application No. 60/891,532, filed on Feb. 26, 2007.

(51) Int. Cl.
*H01J 49/10* (2006.01)
*H01J 49/16* (2006.01)
*C07B 63/00* (2006.01)
*G01N 27/62* (2006.01)

(52) U.S. Cl.
CPC .............. *H01J 49/165* (2013.01); *C07B 63/00* (2013.01); *G01N 27/622* (2013.01)

(58) Field of Classification Search
CPC ........ G01N 27/622; H01J 49/04; H01J 49/06; H01J 49/10; H01J 49/107; H01J 49/165; H01J 49/167; H01J 49/0409
USPC ........................................................ 250/288
See application file for complete search history.

(56) References Cited

U.S. PATENT DOCUMENTS

| | | | | |
|---|---|---|---|---|
| 4,758,721 A * | 7/1988 | Hill | | 250/283 |
| 6,207,954 B1 * | 3/2001 | Andrien et al. | | 250/288 |
| 6,211,516 B1 * | 4/2001 | Syage et al. | | 250/288 |
| 6,806,465 B2 * | 10/2004 | Anderson et al. | | 250/287 |
| 7,091,483 B2 * | 8/2006 | Fischer et al. | | 250/288 |
| 8,080,783 B2 * | 12/2011 | Whitehouse et al. | | 250/288 |
| 2004/0079881 A1 * | 4/2004 | Fischer et al. | | 250/288 |
| 2004/0089802 A1 * | 5/2004 | Kato | | 250/285 |
| 2005/0056776 A1 * | 3/2005 | Willoughby et al. | | 250/281 |
| 2009/0224147 A1 * | 9/2009 | Mie et al. | | 250/282 |

* cited by examiner

*Primary Examiner* — Jack Berman

(57) ABSTRACT

This invention describes an apparatus and method with a combined primary electrospray and secondary electrospray ionization source used to enhance ionization efficiency. The solid phase as well as liquid phase sampling, ionization, and detection is described.

10 Claims, 18 Drawing Sheets

Simulation of 2 mm conductive glass tube as the interface

METHODS AND APPARATUS FOR THE ION MOBILITY BASED SEPARATION AND COLLECTION OF MOLECULES

CROSS-REFERENCE TO RELATED APPLICATIONS

This is a division of application Ser. No. 11/776,392, filed Jul. 11, 2007. The present application claims the benefit of and priority to corresponding U.S. Provisional Patent Application No. 60/807,031 and 60/891,532, filed Jul. 11, 2006 and Feb. 26, 2007 respectively, the entire content of the applications are herein incorporated by reference

BACKGROUND OF THE INVENTION

Enantiomerically pure compounds are of great interest in the pharmaceutical industry and other fields. The rapid and efficient separation and collection of chiral compounds is difficult since they have the same physical properties. All of their physical properties correspond, except the direction in which they rotate plane-polarized light, i.e. they differ in a specific optical activity. Furthermore, all of their chemical properties correspond, except the reactivity toward other chiral compounds. Note that the term chiral compounds are also often used as a general term that refers to the molecules with a chiral center. Development of both preparative and analytical scale separations has provided the tools to determine the enantiomer composition for racemic mixtures, further establishing evidence of the enantiomer rates of activity. Although it has also extended into the agrochemical and food industries, this technology has been primarily driven by the pharmaceutical industry.

The processes traditionally employed for enantiomer preparation, however, suffer from several drawbacks. For example, one process is liquid or gas chromatography. In this process, the analysis mixture is mixed with an externally prepared carrier medium and separated in a separating column as a function of the different affinity of the enantiomers for the stationary phase of the chromatographic column; and thus, the individual components pass in succession through the chromatography column as a function of their different retention times. This process, however, can be very time consuming when multiple samples (such as might be desired in high-throughput screening) are to be analyzed as elution times of 20-30 minutes for one sample, are relatively common. A further disadvantage of the chromatographic process is that the enantiomeric molecules can often have very similar retention times, leading to poor separation per pass.

One of two approaches is typically utilized for chiral separation: 1) indirect and 2) direct separation methods. Indirect separation methods incorporate a reaction between each enantiomer and a chiral molecule to covalently form a new complex, which is then separated from the other enantiomeric complex. This approach is frequently utilized, especially in large-scale operations. Direct methods are based on the formation of non-covalent diastereomeric pairs of molecules using a chiral selector (CS) and rely on differences in the energetics of the complex formation for enantiomer resolution. The chiral selector can either be incorporated into the stationary phase or as an additive in the mobile phase. Chromatography and capillary electrophoresis (CE) have been primarily exploited for chiral separations, both prep-scale and microscale. Typically in chromatography, the stationary phase is chiral (CSP) but chiral additives may also be added to the mobile phase (in liquid chromatography). The first analytical separation of two enantiomers occurred with gas chromatography, but due to the required analyte volatility for gas chromatography, its applications are limited. It is for this reason that liquid chromatography is more commonly employed. In CE, a chiral selector (CS) is added to the electrolyte solution.

Both CE and HPLC have received considerable attention, however, a major difficulty with both techniques is that prediction of the separation conditions remains difficult. For example, in HPLC, there are over 200 CSP's commercially available, yet no clear method to determine which CSP will provide a good separation. This can lead to both time-consuming and costly method development. The fact that HPLC and sometimes CE require longer analysis times (minutes to hours) combined with the lengthy method development creates a real need for analytical tools which either are predictable in the separation capabilities or have faster analysis times, specifically in the early stages of drug development.

SUMMARY OF THE INVENTION

In various aspects, the present inventions provide apparatus and method for separating and collecting chiral molecules using ion mobility, preferably in the gas phase. In comparison to chromatographic separations, gas phase separations can be conducted rapidly, e.g. on the order of milliseconds to tens of seconds as opposed to the tens of minutes typically found in chromatographic approaches. In the case of other compounds which are very similar to each other, for example very similar proteins. These compounds may contain two or more chiral centers that are not related as an object and its mirror image, separation and collection can be enhanced by adding a separating substance where their physical properties are nearly identical.

In various embodiments, the present inventions provide an apparatus for the separation and collection of analyte components in a sample of interest comprising: an ionization source; an ion mobility separator and an ion collector positioned to receive ions leaving the ion mobility separator. The ion mobility separator having an inlet to supply at least one separating substance which comprises particles which to certain degrees selectively interact with at least one analyte component in the sample of interest.

In various embodiments, the ion source employs electrospray ionization (ESI) to form ions. Other methods of ionization and suitable ionization sources include, but are not limited to, matrix assisted laser desorption ionization (MALDI), electrospray ionization (ESI), secondary electrospray ionization (SESI), desorption electrospray ionization (DESI), surface ionization, corona discharge ionization, electron beam ionization, radioactive ionization, photo ionization, laser ionization, laser ablation ionization, direct analysis in real time (DART) ionization and possible combination of multiple ionization principles. In various embodiments, the combined ionization source disclosed in this invention may eliminate ionization suppression in the primary ionization source and enhance over all ionization efficiency.

In various embodiments, the ion mobility separator comprises a device that separates ions on the basis of their mobility through a medium, where the medium is a gas, a liquid, a supercritical fluid, and/or other fluidic materials. It is to be understood, that in the present inventions that this mobility need not be a steady-state ion mobility nor a field independent mobility. The term ion mobility separators (IMS), and ion mobility spectrometers (IMS), includes two broad classes of separators, those that employ a substantially symmetric field (often referred to simply as ion mobility spectrometers although this term is also used to refer to all types of IMS instruments) and those that employ an asymmetric electrical field, often referred to as differential mobility spectrometers (DMS) or field asymmetric ion mobility spectrometers (FAIMS). In the present inventions, both symmetric IMS and field asymmetric IMS can be used.

In various embodiments, the ion collector comprises a moving belt collector. In various embodiments, a moving belt collector includes a belt and accurate motor. Other suitable ion collectors include, but are not limited to, single or multiple Faraday plate, Faraday plate with selective chemical coating, solution phase ion collection, or ion collection/detection method in high vacuum, such as mass spectrometer or electronmultiplier ion detector.

The foregoing and other aspects, embodiments, objects, features and advantages of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

Figure 1:
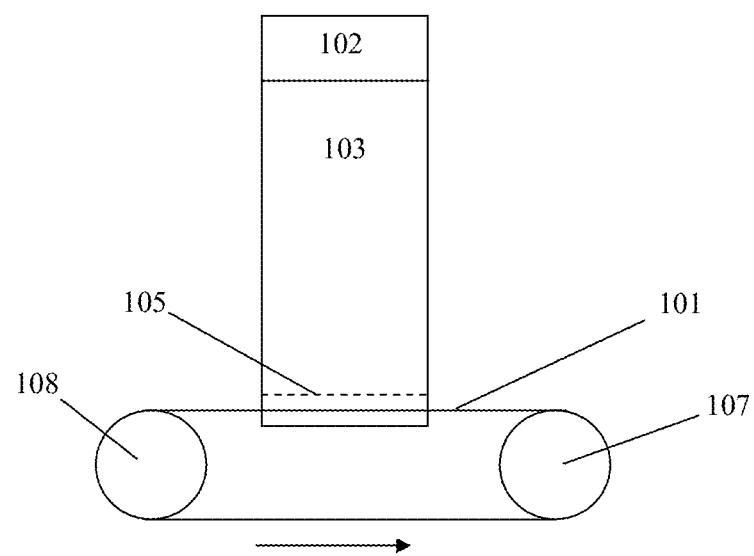
FIG. 1 is a schematic of an example of a moving belt ion collector for sample recovery.

Table 1 shows examples of gas phase enantiomeric separation using IMS-MS; and

Table 2 shows examples of selected chiral molecules.

DETAILED DESCRIPTION OF VARIOUS EMBODIMENTS

Unless otherwise specified in this document the term "chiral" is intended to mean a particle with at least one stereogenic center or chiral center. It should be noted that "chiral" as used herein below may be, but not limited to, chemicals, biologicals, enantiomers, diastereomers, and atropisomers.

The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "separating substance" is intended to mean single or plurality of particle which to certain degrees selectively interacts with single or plurality of analyte component of interest to be separated.

Unless otherwise specified in this document the term "particle" is intended to mean chemical and/or biological single or plurality of atom, molecule, large or macro molecule, nanoparticle, or other matters that are vapor, droplets, aerosol, liquid, solid that follow a mobile medium, where the medium can be a gas, a liquid, supercritical fluid and/or other fluidic materials.

Unless otherwise specified in this document the term "analyte component" is intended to mean various particles, charged particles, and charged particles derived from atoms, molecules, particles, sub-atomic particles, and ions.

In the present invention, one or more volatile chiral compounds (e.g. chiral modifier, also referred to as a separating substance) are infused into the drift gas stream and introduced into the ion mobility separator. Without being held to theory, it is believed that during the analyte-separating substance collisions, transient diastereomeric complexes may form. The hypothesis is that enantiomers can have slightly different equilibrium constants for the diastereomeric complex formation. As the transient diastereomeric complexes formation and deformation process rapidly repeat in the ion mobility separator, stereostructure specific separation of enantiomers can be observed. The contribution of the ion-chiral modifier to the average measured mobility shift should be concentration dependent and analytically quantifiable. The degree of interaction between the enantiomeric ions and the chiral modifiers can also be altered by altering the type and concentration of the chiral modifiers and gas temperature, pressure and flow rate in the drift tube.

IMS may potentially replace chiral SFC and HPLC in the many applications as a chiral molecule separation and collection technique where analysis time is a critical consideration. A more powerful tool can be developed, e.g., based on a chromatography-ion mobility separator-mass spectrometry for characterization of complex mixtures where chiral separation is required. In one aspect, the present inventions provide an instrument with the size comparable to commercial analytical HPLC or SFC. In various aspects, the present inventions provide an IMS system for separation and collection of chiral molecules. A broad range of applications of such a system can be developed to support biomedical research: such a system, e.g., can be used to directly confirm the enantiomeric excess of chiral ingredients in pharmaceutical products; providing, for example, one or more of the following:

1) an increase in the throughput for chirality measurements, specifically in the initial stages of drug development when hundreds of drug compounds are being screened as drug candidates;
2) monitoring of the performance of preparative chiral separation processes, such as SFC and HPLC based separation;
3) detection for chromatography with non-chiral columns; providing, e.g. researchers with more flexibility when choosing chromatographic conditions for the analysis of biomarkers, metabolites or other biological samples; or a detector for chiral chromatograph as a complimentary separation method to resolve enantiomers that cannot be separated by given chiral stationary phase, especially for molecules with multiple chiral centers.
4) preparation of a substantially pure single enantiomer compound The ion mobility base chiral separation methods of the present inventions in various embodiments, can be used for analytical separation, to conduct preparative, semi-preparative separation of chiral compounds or combinations thereof. For example, after being introduced into the gas phase and separation by ion mobility separators, the separated chiral molecules can be collected onto a surface or by liquid solutions. The collection or sample preparation method can be operated as either an online method, a offline method or combinations thereof.

In various embodiments, the methods of the present invention comprise a full profile collection method (FIGS. 1, 3). Profile collections implies collecting samples on-the-fly during mobility separation. For example in one embodiment shown in FIG. 1, after analyte component ions created in ionization source 102, introduced to ion mobility separator through an ion gate as used for analytical purpose IMS. For online collection of from an ion mobility separator 103, a moving belt 101 can be used as the ion collector. An optional ion gate 105 could be placed in front of the moving belt or any other kind of collector for selective collection of ions with a mobility of interest. To operate the moving belt ion collector, motor operable wheels 107 and 108 turning in the range of several thousand RPM may be required. As the ions reach the belt surface, the belt speed is preferably set to correspond with the resolution of the IMS. After the samples are collected on different locations of the belt, the samples can be recollected by dissolving them back in suitable solvents; by separately removing samples from specific locations on the belt, different analyte components can be separately collected. In various embodiments, the belt has marks that correspond to the arrival time in a specific ion mobility separation device and a specific section of the belt can be cut, disassembled, washed, etc., to isolate compounds of interests. For example, a segmented belt could be dissolved back in liquid phase in the same or different solutions. Such recollected sample could be used for, e.g., further chemical analysis.

Figure 2:
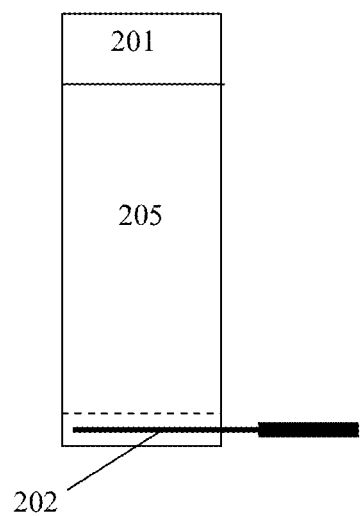
FIG. 2 is a schematic of an example of an access collection plate or plates for sample recovery.

In various embodiments, a selective method (FIGS. 2, 3) can involve collecting samples ionized by ionization sources 201 on a collector 202 from an ion mobility separator 205, and then removing the collected samples from the instrument and, e.g., the separated samples recovered for further study. For example, a metal plate at a set potential can inserted in the spectrometer, and mobility selected ions collected on this plate. The ion mobility separator, e.g., could be a two ion gate TOF-IMS or DMS or FAIMS. In a various embodiments, the analyte components that are separated and collected on the ion collectors, as shown in FIG. 1-3, can be treated with a matrix and further analyzed by MALDI mass spectrometer. Alternatively, the collected samples can be analyzed by mass spectrometer using DART or DESI or other ionization methods. Apparatuses for sample collection after a ion mobility separator, including but not limited to the features described in FIG. 1-3, can be used with a variety of separation devices, separating substance is not necessary to be used with such devices.

Most common ionization sources used for ion mobility and mass analysis can be used to ionize molecules. Electron beam ionization, matrix assisted laser desorption ionization (MALDI), secondary electrospray ionization (SESI), desorption electrospray ionization (DESI), surface ionization, corona discharge ionization, radioactive ionization, photo ionization, laser ionization, laser ablation ionization, DART ionization, and possible combination of multiple ionization principles.

Figure 4:
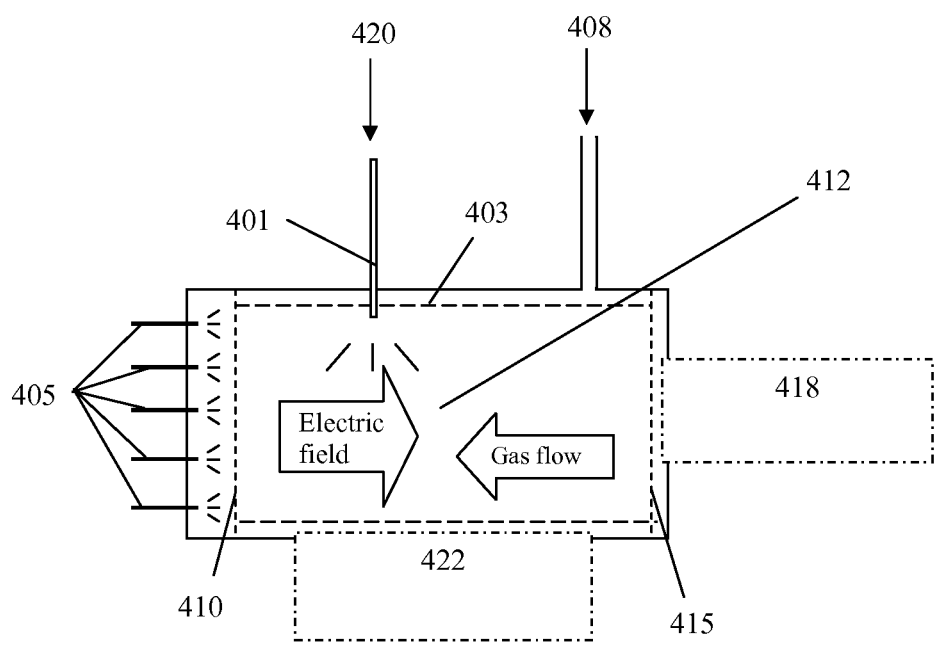
FIG. 4 is a schematic of a combined primary electrospray and secondary electrospray ionization source.

In this invention, a new ionization source is disclosed to enhance to ionization efficiency. FIG. 4 shows a combined ESI and SESI source. The ionization source could be interfaced to the ion mobility separator or mass analyzer 418 and 422 from different angles. In principle, when liquid samples 420 (e.g. eluents from a HPLC) are ionized by the primary electrospray ionization source 401, certain amount of sample in the electrosprayed droplets are not ionized due to limited amount of available charges and surface area. The proposed combined source uses additional electrosprayed (solvent) droplets introduced from separate electrosprayer(s) 405 to interact with un-ionized neutral sample molecules in the ionization chamber 412 to improved ionization efficiency, instrument sensitivity and/or sample recovery efficiency.

In addition, when a mixture of sample is introduced to an ordinary electrospray ionization source 401 (primary ionization) as show in FIG. 4, the samples have higher charge affinity may have a better ionization efficiency; and such high charge affinity compounds may suppress the ionization of other co-existing compounds resulting in certain classes of chemicals that cannot be ionized or suffer from significant sensitivity loss in IMS or MS. The combined ionization source allows separation of ions from high charge affinity compounds from un-ionized low charge affinity compounds by applied electric fields on the guard ring 403 surrounding the ionization chamber 412. After extracting the ionized high charge affinity compounds, the low charge affinity compounds are subsequentially ionized by electrosprayed solvent droplets that are introduced by the secondary ionization source 405 in this region.

The combined source may use one or multiple primary electrospray ionization sources 420 and one or multiple secondary electrospray ionization sources 405, a set of guard rings 403, a gas phase sample inlet 408, ion gates 410 and 415, and interface to mobility or mass analyzer. Ion gate 410 controls the amount of electrosprayed solvent droplet introduced into the source chamber 412. Ion gate 415 controls the timing for ionized sample to be introduced to the mobility or mass analyzer 418. Note the ions can be extracted into an ion mobility separator or mass spectrometer 422 by applying a kick out voltage on segmented guard rings 403; the kick out voltage can force ions in the ionization chamber 412 travel substantially perpendicular to drift direction defined by the electric field before extraction occurred. For liquid phase samples 420, the primary electrospray source introduces charged droplet into the ionization chamber and the droplets are subsequentially desolvated by high temperature gas in the ionization chamber 412. During the desolvation process, sample ions form from the charged droplets. As portion of the sample (low charge affinity samples) are not ionized in this process, they stay as neutrals and flow with the gas toward the secondary electrospray ionization source. Once interacting with the solvent droplets in this chamber, these neutral molecules are ionized via "secondary electrospray ionization" process. The solvent droplets can be introduced into the chamber 412 as a continuous source or pulsed "plug" of charges drifting under the effluence of electric field created by the guard ring electrodes 403. Gas flow rate can be in a range of substantially slow during the ionization and substantially fast during the clean up process. Certain gas flow pattern may be created to suspend neutral molecules or particle of different sizes. As long as the unionized substance stay in the gas flow, they could ionized by the secondary ionization source. When charged droplets, created from such as organic solvents, doped solvents or other liquid mixtures, are introduced into the ionization chamber continuously, maximum ionization efficiency can be achieved by the secondary ionization process. Alternatively, when charged droplets are introduced into the ionization chamber as pulses, each pulse of charged droplets can be used to selectively ionization neutrals with different charge affinities step by step; as the higher charge affinity neutrals extract from the ionization chamber as ions, the next pulse will ionize next high charge affinity neutral. The process can be repeated until all samples in the mixture are ionized. As the ionized samples are all extracted and analyzed using an ion mobility separator or mass spectrometer, the ion mobility spectra or mass spectra could be process and/or reconstructed to provide qualitative and quantitative information about the sample mixture. The analyzers can locate in-line with the guiding electric field 418 or with a designed angle that is from zero to 180 degrees, e.g. perpendicular to the guiding electric field in the source 422. Both primary and secondary electrospray ionized samples are kicked out into the mobility or mass analyzer either sequentially or simultaneously.

Similarly, gas phase sample 408, e.g. eluents from a GC or SFC, can be introduced to the ionization chamber 412 via the gas sample inlet. These samples will interact with the droplet or ions created by the secondary electrospray ionization source and become ionized in this chamber. Note that the secondary electrospray ionization source may introduce ions or charged droplet to the combined source ionization chamber 412 depending on the gas temperature and drying time allowed before ion gate 410. Controlled pulse of solvent ions can be used to ionize chemicals with different charge affinities at different spatial location in the ionization chamber when these chemicals 408 are introduce into the ionization chamber as a pulse of neutral samples.

The ionization process not only depends on charge affinity, the selective ionization mechanism can be used to resolve "suppression" problem in common ionization source based other chemical properties. For example, when $Cl^-$ is doped in the secondary electrospray solvent, the ionization efficiency of chemicals that may form stable chloride adduct could be further enhanced. Not only electrospray ionization source can be used for multiple step ionization operation mechanism, other combined primary and secondary ionization method could also be used to reduce suppression and improve ionization efficiency of mixtures; chemical modifiers can be used in SESI source to create different chemical properties that may selectively ionize compounds of different class with different chemical properties.

Figure 3A:
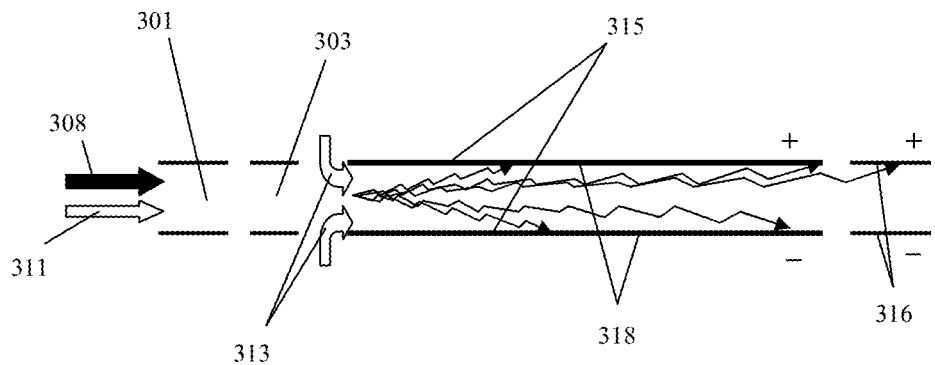
FIGS. 3A and 3B are schematics of a asymmetric IMS for analyte separation and ion collection.
Figure 3B:
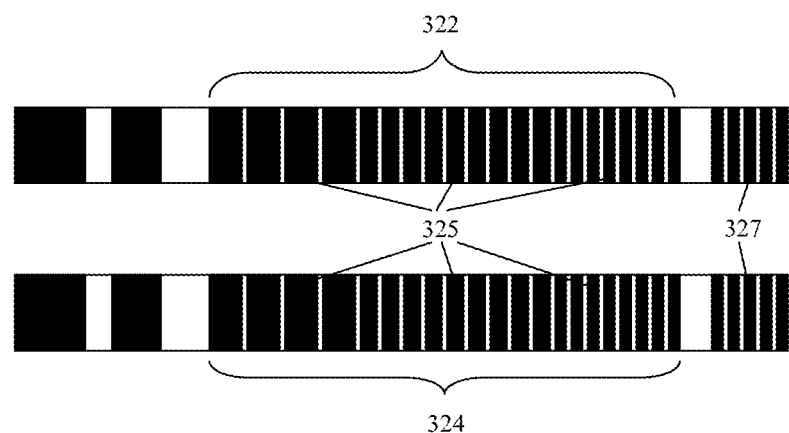

For the asymmetric ion mobility separator, FIG. 3A-B shows similar concept where the secondary ionization is used to enhance the ionization efficiency of the primary ionization source. Voltage offset between primary 301 and secondary 303 sources can help extracting ions formed in the primary source faster then the neutral molecules, where the driving force to move neutral molecules is the gas flow; with the assistance of the electric field, ions can be moved out from the primary source faster then the neutrals. Thus, the suppressed ionization process for molecules with less charge affinities can be resolved similar to the mechanism described in FIG. 4. The combined ionization source could be, but not limited to, an electrospray and secondary electrospray ionization source. It may be advantageous for asymmetric IMS by using a plasma ionization source where both positive and negative ions are generated. Depending on the principle of ionization, sample flow 308 shown in the figure may represent a liquid flow, for electrospray ionization, for example; or a gas flow for radioactive ionization, for example.

Figure 5:
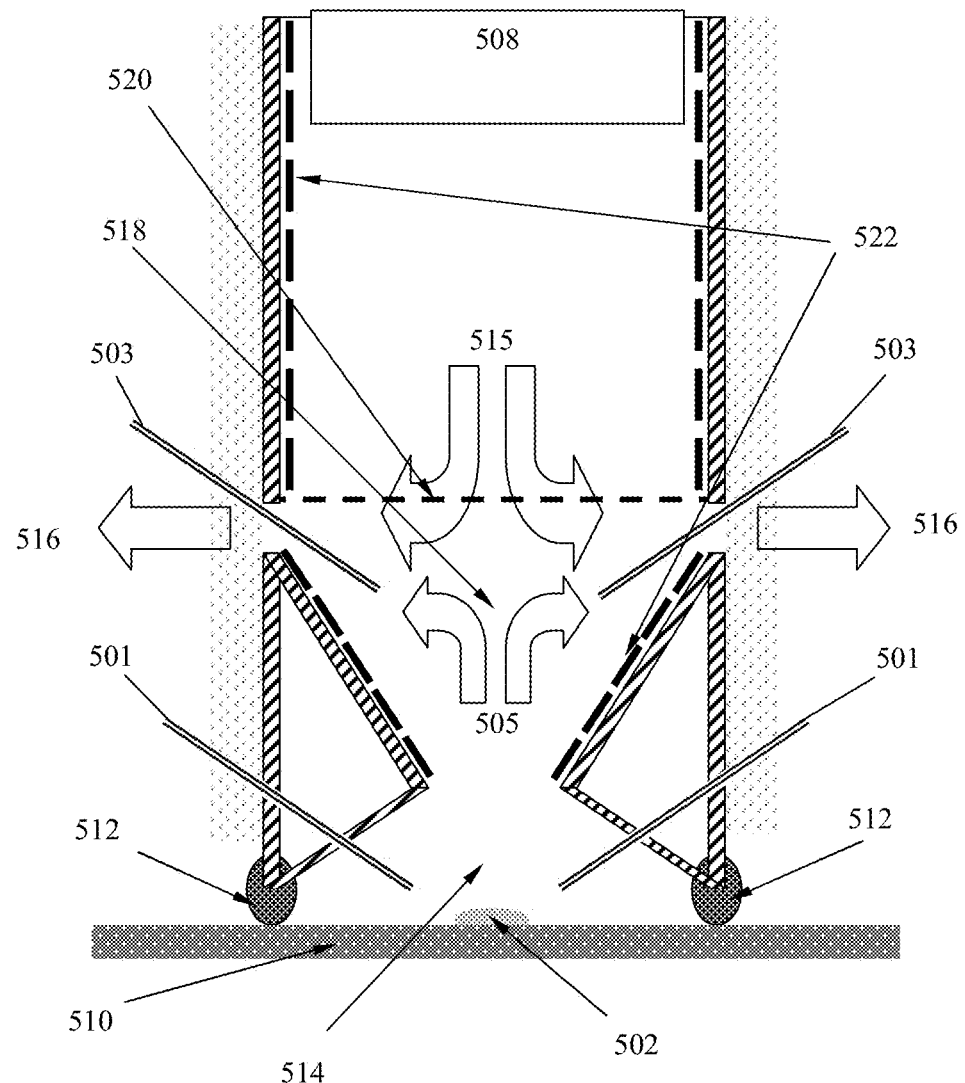
FIG. 5 is a schematic of a solid phase sampling, ionization, and detection process.

Similar to the combined electrospray ionization source, FIG. 5 shows the ionization method for solid samples. In this case the primary ionization source 501 can be desorption electrospray ionization (DESI), Direct Analysis in Real Time (DART) ionization, laser ablation/desorption ionization, MALDI and other method for ionization of solid samples. The secondary ionization source 503 can be SESI or other gas phase chemical ionization methods. For solid samples 502, air flow may be added to assist removing samples away from a surface. When the sample is desorbed from the surface as ions in the primary ionization region 514, the ions are extracted into secondary ionization region under influence of gas flow 505 or electric field, or both; the electric field is created by guard rings 522. When the sample on the surface is desorbed as neutral molecules, they are extracted into the secondary ionization region by gas flow 505. Depending on sample's physical and chemical properties, the secondary ionization source may employ a variety different kind of charged droplets (that could be altered by chemical modifiers) to interact with the sample that has been brought into the gas phase. As shown in this figure, secondary electrospray ionization process is the main mechanism for the secondary ionization; alternatively, for relative small molecules, atmosphere chemical ionization (APCI) may be used as the secondary ionization mechanism. In various embodiments, other ionization methods, such as photo ionization, electron beam ionization or laser ionization can also be method of choice for secondary ionization.

FIG. 5 illustrates an example of the solid phase sampling, ionization, and detection process. Sampling target 510 is a surface where the sample 502 of interest may be located on. The sampling and detection apparatus may also have a sealing material 512 when it is intended to be used as in contact with sampling target, however, non-contact sampling is preferable in many application of this apparatus. For instance, when DESI method is used as the primary desorption/ionization method, both ionized and neutral molecules are extracted from the surface and brought into the secondary ionization region 518; in this area, the charged solvent droplets introduced by the SESI source 503 interacts with the neutral molecule by either dissolving them in to the solvent droplets or transferring charges to these molecules. The ionized samples are introduced to an IMS through an ion gate 520. The unionized neutral molecules, carrier gas 505, and drift gas 515 from mobility separator are exhausted 516. As a result, the combined ionization source can enhance the ionization efficiency beyond the primary ionization methods alone. Alternatively, after the secondary ionization process, ions can also be introduced to a mass analyzer 508; the mass analyzer can either located at the end of an ion mobility separator, as shown in FIG. 5, or directly mounted to the combined ionization source.

In a symmetric IMS device (sometimes referred to as TOF-IMS), a propelling DC field gradient and a counter gas flow are set and an ionized sample is released into the field which flows to a collector electrode. Ion species are identified based on the DC field strength and time of flight of the ions to the collector. At low values of E/N ion mobility is typically a constant value, where E is the electrical field and N is the gas density (often referred to as number density) in the drift tube.

Time of flight ion mobility spectrometry is a gas phase analytical technique that separates ions based on both size and shape. In IMS, ions are created and then subjected to an electric field, causing the ions to accelerate through the ion mobility drift tube while colliding with neutral drift gas molecules (typically an inert gas such as nitrogen). As the ions travel through the drift tube, they undergo random collisions and accelerations until reaching the end of the drift region, where they are either detected by a Faraday plate or transmitted through an interface to a mass spectrometer where they are mass separated and detected. An ion's mobility through the drift tube is defined as the ratio of the average ion velocity ($v_d$) to the applied electric field (E) (when operating in the low-field region). IMS then takes advantages of mobility differences to separate ions.

Experimentally, an ion's mobility (K) can be determined by the following equation:

$$K = \frac{v_d}{E} = \frac{L^2}{t_d V} \quad (1)$$

where L is the length of the drift region, $t_d$ is the time the ion travels through the drift region (drift time), and V is the voltage applied to the drift region. The ion mobility can be related to the ion-drift gas collision processes at the molecular level by the following:

$$\Omega = \left(\frac{3}{16N}\right)\left(\frac{2\pi}{\mu kT}\right)^{1/2}\left(\frac{ze}{K}\right) \quad (2)$$

where $\Omega$ is the average ion-drift gas collision cross section, z is the number of charges on the ion, e is the charge of one proton, N is the number density of the drift gas, $\mu[=mM/(m+M)]$ is the reduced mass of an ion (m) and the neutral drift gas (M), K is the ion mobility and k is Boltzmann's constant. When the experimental parameters are held constant, the mobility is dependent on the ion charge, the ion-drift gas reduced mass and the collision cross section as follows:

$$K \propto \frac{z}{\Omega\sqrt{\mu}} \quad (3)$$

For ions more massive than the drift gas molecule, the reduced mass is nearly equal to M and the mobility is primarily proportional to z and $\Omega$.

Assuming that the ion is more massive than the drift gas molecule and that the ion charge can not be altered, a change in the ion mobility would require a change in the collision cross section. The collision cross section term is a function of the interaction between the ion and the neutral drift gas molecule, the collision dynamics and the size and shape of the ion and neutral molecule. The drift gas can be thought of as a weak stationary phase for the ion mobility experiment and by adjusting the stationary phase, the separation characteristics can be adjusted. The collision cross section can be altered by changing the drift gas, both due to the size contribution of the drift gas and the degree of interaction between the ion and neutral molecule. Varying the temperature of the experiment can also affect the interaction between the ion and neutral molecules.

In an asymmetric IMS device, ion species are identified by mobility behavior in a high asymmetric RF field, where ions flow in a carrier gas and are shifted in their path by an electric field. Various asymmetric IMS devices operate with a selected RF field at Vmax and species detections are correlated with a pre-set, or scanned, DC compensation voltage (Vc). Species are identified based upon correlation of Vmax and Vc with historical detection data. For a given ion species in a sample, as the amplitude of the asymmetric RF voltage (at Vmax) changes, the amplitude of the DC compensation voltage (Vc) required for passage of that species through the filter field also changes. The amount of compensation depends upon species characteristics.

Various asymmetric IMS devices include a pair of opposed filter electrodes defining a gap between them in a flow path (also known as a drift tube). Ions flow into the analytical gap. An asymmetric RF field (sometimes referred to as a filter field, a dispersion field or a separation field) is generated between the electrodes transverse to the carrier gas/ion flow in the gap. Electrical field strength, E, varies as the applied RF voltage (sometimes referred to as dispersion or separation voltage, or Vrf) and size of the gap between the electrodes. Such systems can operate at atmospheric pressure.

Ions are displaced transversely by the RF field, with a given species being displaced a characteristic amount toward the electrodes per cycle. DC compensation (Vc) is applied to the electrodes along with Vrf to compensate for the displacement of a particular species. The applied compensation is used to offset the transverse displacement generated by the applied Vrf for that particular ion species. The result is zero or nearzero substantially transverse displacement of that species, which enables that species to pass through the filter for detection. All other ions undergo a net displacement toward the filter electrodes and eventually undergo collisional neutralization on one of the electrodes.

If the compensation voltage is scanned for a given RF field, a complete spectrum of ion species in the sample can be produced. The recorded image of this spectral scan is sometimes referred to as a "mobility scan", as an "ionogram", or as "DMS spectra". The time required to complete a scan is system dependent. Relatively speaking, a prior art IMS scan might take on the order of a second to complete while and a prior art DMS might take on the order of 10 seconds to complete.

An asymmetric IMS operates based on the fact that an ion species will have an identifying property of high and low field mobility in the RF field. Thus, an asymmetric IMS detects differences in an ion's mobility between high and low field conditions and classifies the ions according to these differences. These differences reflect ion properties such as charge, size, and mass as well as the collision frequency and energy obtained by ions between collisions and therefore enables identification of ions by species.

In various aspects, the present inventions employ asymmetric IMS to separate chiral molecules, a similar approach as described for the symmetric IMS is used. FIG. 3A schematically illustrates an overview of such a device and method. A chiral modifier or chiral modifiers are introduced to the device from either the sample flow inlet 311 or an additional gas inlet 313 located between ionization source and the ion mobility separator or from both inlets. The IMS separator can, for example, be two parallel plates 318 (as shown in FIG. 3A), concentric cylinders, or other shapes. The ion mobility separator can be used for, for example, analytical purposes, preparative purpose or both. For analytical purposes, in various embodiments, separated chiral molecule(s) are collected on a different set of electrodes 316 after passing through the mobility analyzer. For preparative purpose, in various embodiments, the mobility analyzer plates can also be used as ion collectors; and compounds with different mobility properties can be collected a different location on these plates. These compounds can be recovered after the separation process. This practice is not limited to chiral separation; it can be used to recover samples for general chemical isolation purposes without chiral modifier or any other separating substances. The collector plates can be made of, but not limited to, metal plates or metalized non-conductive plates. Each of these plates can have one or multiple electrodes for ion collection and generating electric field for ion separation. FIG. 3B shows the surface of upper 322 and lower 324 ion collection plates of a parallel plate asymmetric ion mobility separator, where multiple electrodes 325 and 327 are used in ion mobility separator and detector region, respectively. The electrodes on ion mobility separator plates 318 (FIG. 3A) can be segmented in uneven sizes according the mobilities of targeted analyte components and the resolution required. These electrodes can be individually set to different voltages or removed from the sample collection. The multiple electrode approach can provide the capability of setting different dc or rf potentials to enhance mobility based separation.

Similar to the moving belt configuration for the symmetric IMS, the preparative collection plate (e.g. FIG. 2 item 202 and FIG. 3A item 318) can be removed from the device and cut into slices according to the spatial separation of the samples of interest. Slices of collected sample can be dissolved in solution for further investigation or study. Alternatively, the collection plates can also be directly analyze by MALDI-, DESI-, DART-, other ionization method with either mass spectrometers or ion mobility spectrometers; the collection plates can also be further analyzed by other spectroscopic methods, including but not limited to NMR, IR, UV-Vis methods. For selective collection purpose, the ions of interest can also be collected on different sets of plates 316 that are used as the ion detector for analytical asymmetric IMS. The selective collection plate can also be segmented and have electrodes to enhance the selectivity by spatially removing overlapping samples on the collective plate.

An underlying principle for separating and collecting chiral and nonchiral molecules in the asymmetric IMS is the gas phase selective interaction between chemical modifiers and the analyte components of interest. In an asymmetric IMS device, the time for such interaction is during the CV applied period. During this period of time, the ions are at low E/N conditions. The asymmetric IMS is preferably operated to have an extended CV period compared, for example, to traditional DMS and FIAMS device operation. In various embodiments, the CV period is 1150 ns where 37,500 collisions may occur under ambient pressure conditions.

In various embodiments, operating conditions such as, but limited to, pressure, temperature, electric field strength, and carrier or drift gas flow rate. For example, operation of the ion mobility separator at a relatively low pressure, e.g., about 1 to about 700 Torr, can provide for an easier interface to a MS, however it is preferred that the gas phase concentrative of chiral modifier is adjusted to achieve similar separation performance to higher pressure operation.

Above described ion mobility base chiral separation methods of the present inventions in various embodiments, can be also used for the separation of nonchiral compounds; in this case, the chiral modifier can be replace with other chemical modifiers that selectively interact with analyte components of interest. The sample collection methods already described in previous sections can be used to collect these compounds. For example, separation of stereoisomers, such as proteins and lipid, that can be enhanced by adding a separating substance where their physical properties are nearly identical. If, for example, two proteins having very similar drift times are to be separated from each other in an ion mobility separator, a suitable separating substance can be selected which is known to have a significantly greater interactive cross section with one of the protein molecules than with the other protein. The sample collection methods already mentioned can be used to collect these compounds.

In various embodiments for symmetric IMS, an ion focusing method can be employed to guide ions to a target collection area on the collector. Suitable focusing methods may include, but are not limited to, static electric field focusing and ion funnel focusing. An ion collector can be segment to facilitate, e.g., collection of ions with specific ion mobility (drift time) or a certain range of mobilities on to different segment of the ion collectors.

Figure 6:
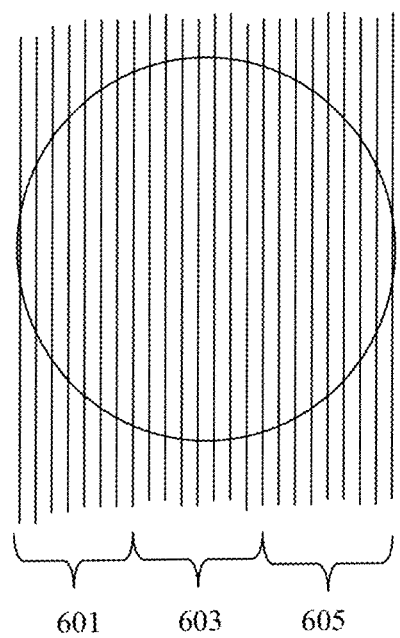
FIG. 6 is a schematic example of a segmented Bradbury-Neilson gate for ion collection.

In various embodiments of IMS instruments, wherein the Bradbury-Nielson gate can be segmented. A variety of geometries, including but not limited to parallel, rectangular, concentric ring shape, can be used for the segmentation, referring to FIG. 6, various embodiments can use parallel segmentation. Each segment of the ion gate, for example, 601, 603, and 605, can be controlled to open at a different time. Such a segmented ion gate can be used as either first or second ion gate in a time-of-flight type ion mobility separator. While it is used as the second ion gate in a IMS, multiple portions of ions with different drift time are allow to pass through segmented ion gate, thus collected on different section of ion collectors, and recovered separately if desired.

In various embodiments, an apparatus of ion gate for an ion mobility separator comprising a segmented Bradbury-Nielson that contains multiple sections of Bradbury-Nielson gate. The segmented Bradbury-Nielson gate can be used as a second gate in a time-of-flight type ion mobility separator. The segmented Bradbury-Nielson gate comprises a variety of geometries which may include but is not limited to: parallel, rectangular, concentric. The ion mobility separator further comprises a segmented ion collector where a plurality of sections of ion collector is inline with the sections of the segmented Bradbury-Nielson gate.

The collection surface for an ion collector of the present inventions can be, for example, a solid surface. This surface can be coated with different materials to facilitate collection, removal, detection, etc. The surface can be set at an appropriate potential to electrically neutralize (convert ions to neutrals) ions collected thereon. The surface can be, e.g., a metal belt, a metalized non-conductive material, such as ceramic or polymers, or combinations thereof. FIG. 1 shows a schematic of moving belt 101 configuration and FIG. 2 shows a schematic of a configuration having an accessible ion collector plate 202. Coating materials, applied, for example, to the belt or plate, can be used to enhance the usability of the collection method. For example, a collector coated with a chemical agent that can form a chemical bond, e.g., covalent bonds, with ions of interest can be used to the enhance the selectivity of the separation and purification process; such collector can, e.g., be chemically washed to removed unwanted interferences, thus only sample that had right mobility properties and chemical reactivity toward the coating material will be left on the plate. Any chemical agent, or a portion thereof, that remains attached to the analyte component of interest can later be removed for further investigation.

An ion mobility separator and methods of use thereof, of the present inventions, can use a liquid phase, e.g., a solution, as an ion collection device. Such a solution, or solutions, can be static, for example, retained in a container or can be dynamic, for example, flowing on a surface. An electrical potential can be applied to the solution or solutions, e.g., to facilitate an ion neutralization, collection, or reaction with a chemical agent in the solution(s).

The collection solution can be conductive or non-conductive. With a conductive solution, e.g., a voltage can be applied to the solution and ions can enter the solution directly, so, in various embodiments, the solution can behave like a solid. For a non-conductive solution, other effects can be used to assist the ion collection. Such effects include, but are not limited to, gas flow toward the collection solution, a high electric field ion acceleration in front of collection solution, and usage of a polarizable liquid. After ions of interest are collected in the solution, the solution can be removed from the IMS device and used, e.g., for further investigation subject to purification, etc. The ion collector can use more than one collection container with different solutions. Sample solution or solutions can contain a reagent (e.g., chemical agent) that may be reactive to the ions to be collected; on-the-fly reactions between collected ions and the added reagent, or the solutions themselves, can be accomplished in the IMS device. The collected samples, e.g., can be used for further analysis, such as IR spectroscopy, NMR spectroscopy, and MS, for synthetic reactions, etc. The collected samples can be used to prepare a pharmaceutical formulation.

In various embodiments of a static collection solution, mobility selected samples are collected into the solution for a period of time and the solution is removed from the device for further investigation and/or use in various embodiments of a dynamic collection solution, the solution moves on the surface. The movement of the liquid can be either across the surface, flow inside, flow outside of the surface, or combinations thereof. The fluid can be mechanically moved, e.g., by creating a pressure difference, by electroosmotic force, etc. In various embodiments, a micro-machined collection plate, having multiple channels for liquid flows can be used. With the dynamic solution collection methods, the collected flow can be led to a flow cell or other fluid guides of any kind to communicate with other instruments.

With a preparative IMS, a sample is first prepared in a suitable format, gas, liquid, solid phase, for example, or combinations thereof. A sample is introduced to the ionization source where it is ionized; subsequently the ionized sample is separated by a mobility separator. The sample can be a mixture of many different molecules and chiral molecule(s) thereof. The mobility separated sample can be collected on a full-profile collector, such as a moving belt, selectively collected on a partial collector, such Faraday plates or collection solutions or combinations thereof. For example, ions corresponding to molecules not of interest could be collected in a static manner, e.g., all on substantially the same solution or location on a belt. The ion collector could then be operated in a dynamic mode, for example moving a belt, flowing solution, etc., to separately collect samples, e.g., different chiral molecule(s) of interest. After the samples are collected on the collector for certain amount of time, they are removed from the IMS and reused in their pure form.

Figure 7:
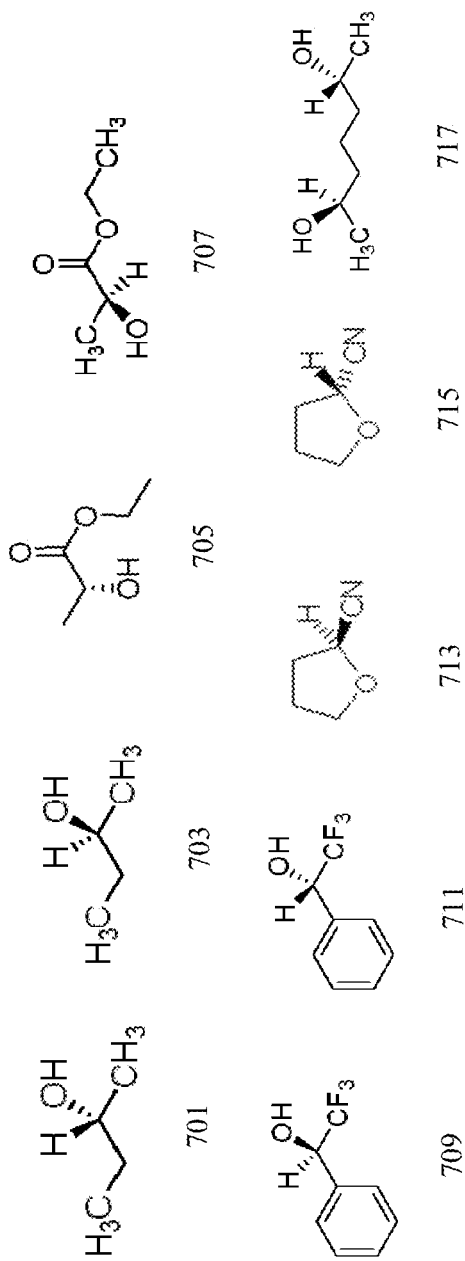
FIG. 7 shows examples of chiral modifiers (separating substances)

Selecting an effective chiral modifier (also referred to as a separating substance herein) for the ion mobility separator can be accomplished as follows. Without being held to theory it is believed that the interaction force among chiral molecules may involve hydrogen bonding, dipole-dipole, $\pi$-$\pi$, acid/base, stereo-repulsion, etc. As illustrated in the Examples of the present application, R- and S-2-Butanol can be used to separate enantiomeric mixtures. Without being held to theory it is believed that the primary force for a butanol based chiral modifier is hydrogen bonding. In various embodiments a series of chiral modifiers, examples are as shown in FIG. 7, are selected for separation of targeted bioactive chiral molecules. The modifiers are chosen to demonstrate different possibilities of gas phase interactions. Accordingly, it is to be understood that suitable chiral modifiers for the present inventions are not limited to those specifically shown.

Among gas phase interaction forces, gas phase hydrogen bonding is typically the strongest; and the addition of other interaction forces may further enhance the chiral based separation. Using (R)-(−)-2-Butanol 701 and (S)-(+)-2-Butanol 703 as a baseline study, see FIG. 7, we choose (R)-(−)-$\alpha$-(Trifluoromethyl)benzyl alcohol 709 and (S)-(+)-$\alpha$-(Trifluoromethyl)benzyl alcohol 711 for its possible $\pi$-$\pi$ interaction; (R)-Tetrahydrofuran-2-carbonitrile 715 and (S)-Tetrahydrofuran-2-carbonitrile 713 for its possible stereo-hindrance effects; (2R,6R)-2,6-Heptanediol 717 for its symmetric multiple chiral center interaction; (+)-Ethyl D-lactate 705 and (−)-Ethyl L-lactate 707 for its enhancement of hydrogen bonding, as these molecules can be a hydrogen bond donor as well as acceptor. Using the principles of the present application a larger selection of the chiral modifiers can be screened to build a knowledge base for chiral modifier selection and/or choice are based on different interaction forces.

In the separation and collection process, multiple chiral modifier gases can be used simultaneously, sequentially, in turns or combinations thereof. The instrument design for the IMS can include, e.g., a fast switch mechanism to infuse different a chiral modifier one at a time, selective chiral modifiers at the same time, or combinations thereof in to the IMS.

The fast switch mechanism is preferred for rapid chiral separation and collection using IMS. Different chiral modifier gases are preferably switched from one to another within seconds or minutes and typically the effectiveness of the separating substance can be observed within same amount of time. The chiral modifier concentration during the ion mobility separation process can either be set to a substantially constant or change with time. A chiral modifier concentration gradient in the IMS can be used, e.g., to alter the separation characteristics. By this means, e.g., a sequence of mobility spectra could be obtained under different chiral modifier concentration conditions. A software module can be used to monitor the ion mobility peak shifting and other characteristics of the chiral molecule ions. The separation and collection of chiral molecule structure can be tracked, e.g., by the software to find preferred separating conditions. Similarly, a pressure or temperature gradient, together with the chiral modifiers), can be used in the ion mobility separator to further refine or alter separation and collection conditions.

In addition, it is important to note that the mobility based separation happens in an ion mobility separator, any reactions, such as charge transfer or cluster formation, between chiral molecule ions and chiral modifiers can cause ion mobility peak broadening and may produce unpredictable results. Charge transfer in the ion mobility separator is a major concern, thus, chiral molecules with relatively weak charge affinity are preferably chosen. Similarly, less reactive chiral molecules are preferred instead of those that form a stable complex that may permanently convert the targeted chiral molecule(s) to another chemical form. In various embodiments, the chiral modifiers can be chosen to selectively react to one of the chiral molecule(s) in the mixture. In various embodiments, such a reaction can occur in the ionization source, and the separation in IMS can become separating one chiral molecule from the other chiral molecule in the cluster. This approach, in various embodiments, can provide a means for determining the chiral structure (S-, R-, L- or D-) of the molecule since the chiral modifier structure is known.

The ion mobility separator described in the present inventions can be interfaced with a chromatographic separation method, e.g., a supercritical fluid chromatography (SFC), high performance liquid phase chromatography (HPLC), electrophoresis systems, etc. With the combined ionization sources described herein, elutents from an HPLC, electrophoresis systems, etc., can be directly electrosprayed into the IMS device; and the elutents from SFC or GC can be introduced to the heated gas sample inlet of the ionization source (see e.g. FIG. 4 item 408).

The IMS systems and methods of the present inventions can be powerful tools for chiral separation and collection; combining with chromatographic system can open a broad range of instrumentation. For example, using chiral separation IMS with non-chiral chromatographic or electrophoresic systems can facilitate the separation of complex mixtures with a more flexible choice of stationary phases, mobility phases, and other chromatographic or electrophoresic conditions. The chiral separation and collection IMS device can be linked with a chiral separation chromatographic or electrophoresic systems to further purify the chiral molecule(s) of interest. For complex mixtures, for example, interfacing chromatographic or electrophoresic systems to ion mobility separator, and to mass spectrometric systems can provide a powerful tool for analytical and preparative separation.

The IMS based chiral separation methods of the present inventions can also be used to monitor other preparative or semi-preparative chiral separation methods, such as, e.g., SFC and HPLC methods. For example, by splitting the flow in these systems to the IMS, IMS can provide an online monitoring method for the preparative separation method.

IMS-MS provides a powerful tool for sample analysis. The ion mobility separator can be interfaced to, but limited to a quadrupole, an ion trap, or time of flight mass spectrometer. Existing IMS-MS interfaces typically suffer from low transportation efficiency. The present application provides unique IMS-MS interface designs that facilitate overcoming this limitation of traditional interfaces.

Historically, the ion transportation rate of an IMS-MS is one of the bottlenecks for instrument sensitivity. Because of the large pressure barrier between IMS and MS operating conditions, effective transport of ions from the IMS to the MS through an open interface with minimal time delay has been difficult. The present application, provides several interface designs. The interface described in this invention can be used independently from rest of the instruments and methods described in this invention.

Figure 8:
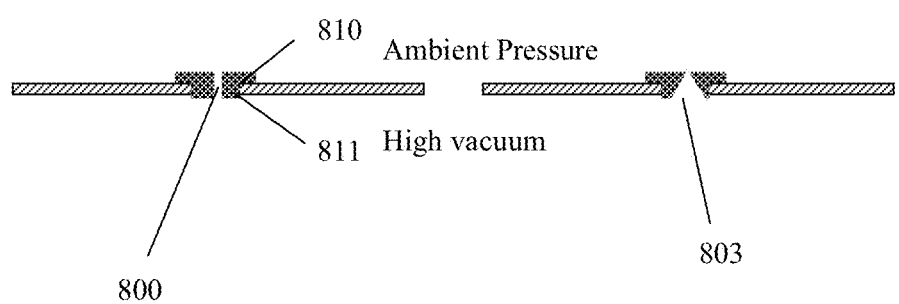
FIG. 8 shows examples of various embodiments of ambient pressure and vacuum interfaces for sampling ions from ambient pressure.
Figure 9:
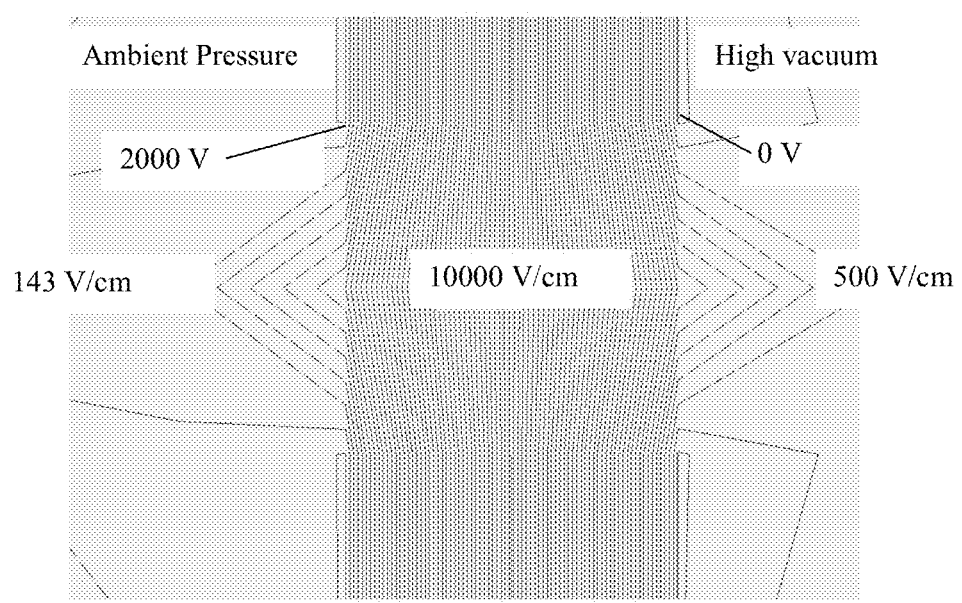
FIG. 9 shows simulation of equal potential lines for a 143 V/cm (100V over 0.7 cm), 10000 V/cm (2000V over 2 mm) inside the resistive interface.

In one aspect, the present inventions provide an interface using high field ion extraction with short resistive glass tube or pinhole interface 800. Resistive pinhole or resistive capillarity tube interface 800 of the present inventions can be used for transporting ions from atmospheric pressure to high vacuum. For example, conductive glass from Burle Industry can be used for a glass capillary tube. Examples are shown in FIG. 8 where first voltage 810 and second voltage 811 are applied across the tubing or pinhole. The size and shape of the resistive interface is made to maximize the ion transportation. An alternative shape of the resistive interface 803 is shown in FIG. 8. Simulation of the electric field is shown in FIG. 9. The resistive glass tube can be used to generate a high electric field inside the pinhole and the electric field strength inside and outside the pinhole can create a local focusing effect that can bring more ions into the vacuum. Multiple resistive tubes or pinholes, e.g., in parallel, can be used on the same device to enhance the sensitive. Resistive glass is one material that can withstand the temperatures typically required for an IMS-MS interface. Beyond the electric field created in the pinhole region, the ion focus electric field can be extended to further distance for the local pinhole region, in order, e.g., to focus more ions into the pinhole region, and thus transport them into the vacuum chamber for mass analysis In various embodiments, the interface between an IMS and MS uses a resistance tube; and a high voltage power supply operatively connected to the resistance tube. The resistance tube has an inner diameter in the range between about 1 micrometer and about 2 mm and the high voltage power supply is configured to apply a voltage gradient in the range between about 1 and about 40,000 volts across the inner diameter of the resistance tube.

Figure 10:
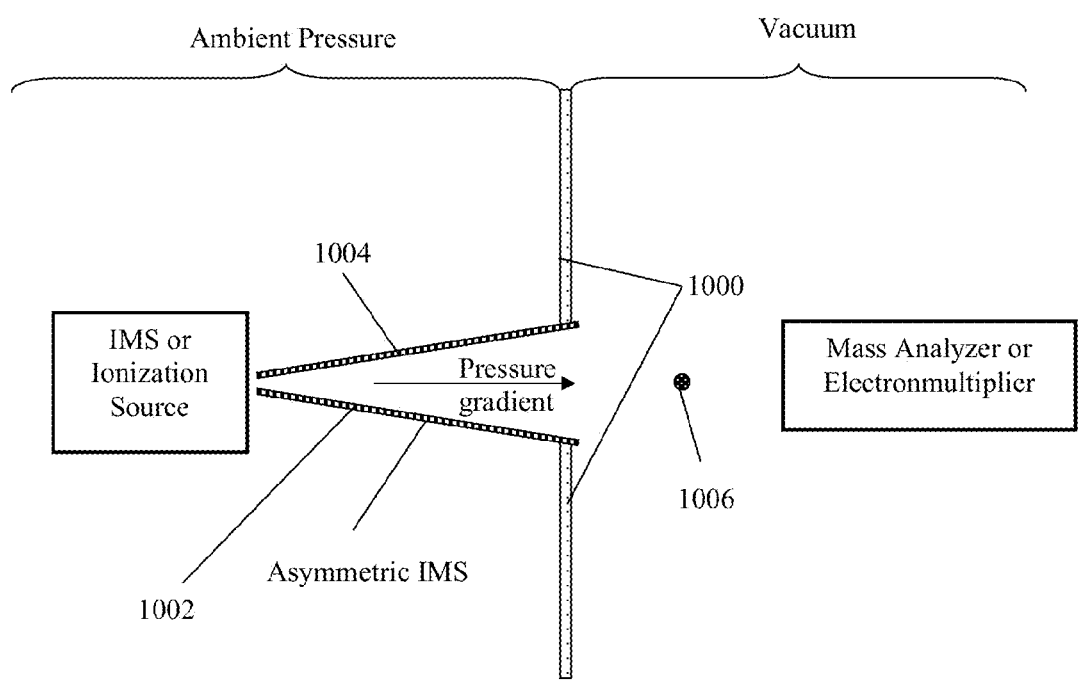
FIG. 10 shows a schematic example of an embodiment of asymmetric IMS with the pressure gradient in the device serving as the interface of the mass spectrometer for the sampling of atmospheric ions. The interface can be used, e.g., to sample ions from IMS or directly from atmospheric ionization sources.

In one aspect, the present inventions provide an interface using a transverse electric field at the interface 1000 of the ambient pressure and vacuum region (FIG. 10). The two conductive plates 1002 and 1004 are arranged with a small angle that is equal or greater than zero degree; the E/N ratio is preferably kept substantially the same in this interface by balancing the pressure gradient and distance between these two plates. In various embodiments, an electric field correction electrode 1006 can be placed at a location outside the interface 1000 with an appropriate potential with respect to the plates. Similar arrangements can be achieved in the cylindrical fashion. Alternatively, the segmented electrodes on non-conductive plates can also be used to create similar transverse electric field that could function as asymmetric ion mobility separator at the IMS-MS interface. The segmented plate (electrode) approach provides flexible control parameters. The asymmetric ion mobility separator interface could also be optimized for ion focusing during the ion transportation in the IMS-MS interface.

The interface between an IMS and MS uses a first conductive member and a second conductive member, wherein the first and second conductive members are substantially symmetrically arranged about an ion transport axis and wherein the distance between the ends of the first and second conductive members proximal to an ion mobility separator is equal or less than the distance between the ends of the first and second conductive members distal to the ion mobility separator and a DC and RF power supply operatively connected to one or more for the first and second conductive members. The first and second conductive members are plates. The DC and RF power supply is configured to apply voltages between the first and second conductive members in a means that is resemble to the operation of an asymmetric ion mobility separator with two parallel plates, where the first and second conductive members are closest.

Figure 11:
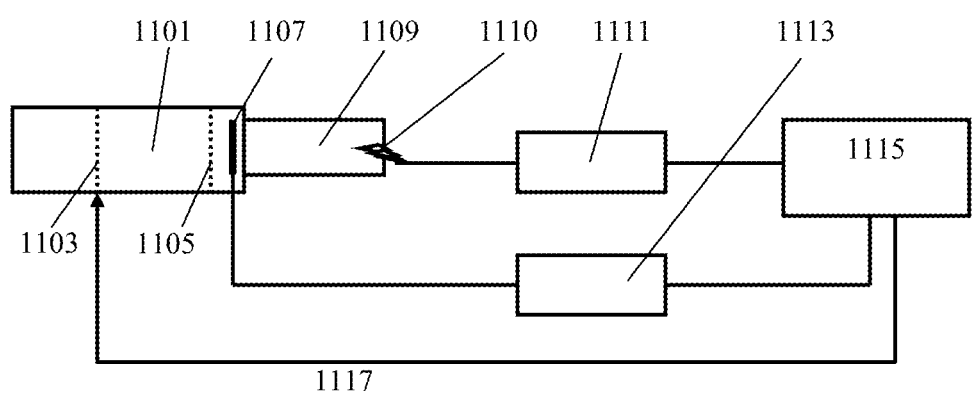
FIG. 11 shows a schematic example of a data acquisition scheme for an IMS-MS systems. Ion Gate1 and Gate 2 are designed to select an ion of interest and to deposit such on the sample collector, direct to a mass spectrometer for further analysis or both. Ion mobility spectrometer and mass spectrometer data can be generated through two separate channels and correlated in the data acquisition software.

For IMS-MS analysis, ion mobility is preferably measured outside the vacuum chamber (under a uniform pressure conditions) for better mobility resolution and increased accuracy. FIG. 11 schematically illustrates using measured mobility outside the vacuum chamber to, for example, correct mobility measured inside the vacuum chamber with a MS. With common MS design, addition drift time is added to the mobility measurement when using MS as a detector; ions have travel through a pressure gradient in the IMS-MS interface and low vacuum ion optics where addition collision occurs. With the IMS-MS system shown in FIG. 11, a control and data acquisition module locates on a computer 1115; Signals 1117 communicated to the ion mobility separator 1101 control the first gate 1103 and second gate 1105 of the ion mobility separator, at least a portion of the ions are allow to enter the ion mobility separator and then allowed to pass through the second gate 1105. Drift time (or mobility) of ions are first measured at the ion detector/collector 1107; the measured ion signal is processed with preamp 1113 and the data acquisition modules on the computer 1115; After a portion of the ions travel through the IMS-MS interface, and then mass separated in MS 1109 and detected on the MS ion detector 1110. The measured ion signal is then process with preamp 1111 and the data acquisition modules. Ion mobility spectra generated at ion detectors 1107 and 1110 are processed by the data acquisition module and mobility correction can be made for each individual ions based on their mobility measured outside the vacuum chamber. In various embodiments, a software module can be used to realize such correction/calibration. This procedure is preferred when using an ion collector outside the vacuum chamber for sample collection and MS for ion monitoring and identification.

In various embodiments, the ion detector 1107 used to measure ion mobility outside the vacuum chamber, could also be used as an ion collector that collects at least a portion of the samples for further analysis or other use. In various operation mode of the IMS-MS device, selected ions may be allowed to pass the second ion gate 1105. As a large portion of the selected ions are collected on the ion collector 1107, a small portion of the selected ions may be detected by the MS to identify their mobilities and mass to charge ratio. Similarly, when asymmetric ion mobility spectrometer used as ion mobility separator, selected ion are allowed to pass through the IMS and detected either on the ion detection/collection plates 316 or a MS located in the vicinity of the detection plates, the rest of the ions are collected at different location of the full profile ion collection plate 325. In various embodiments, the instrument operating parameters, e.g. compensation voltage and RF frequency, may be used to correlate the location of ions collected on the full profile ion collection plate and ions detected by the MS or ion detection plates.

If the drift time measured outside the vacuum chamber is $t_{out}$ and the m/z data is acquired at $t_{ms}$, then the measured m/z data can be correlated to the mobility data by the factor of a delay time in the interface for each individual ions.

If the drift time measured outside the vacuum chamber is $t_{out}$ and the m/z data is acquired at $t_{ms}$, then the measured m/z data can be correlated to the mobility data by the factor of a delay time in the interface for each individual ions.

The method for operating an ion mobility separator and a mass spectrometer may include: (a) measuring ion mobility of an analyte component using an ion detector/collector at the end of the ion mobility separator; (b) measuring ion mobility and mass to charge ratio using ion detector of mass spectrometer; (c) correlating the ion mobility data obtained from mass spectrometer with the ion mobility dada from the ion mobility separator. The ions collected on the ion collector at the end of the IMS are mass identified using the correlated ion mobility data.

The IMS-MS instrument of the present inventions can be operated, in various embodiments, as a combined preparative or analytical chiral separation and sample recovery system. For example, with segmented or un-segment Faraday collection plates mounted in the front of MS, a majority of the sample separated by the IMS can be collected on the Faraday plate(s) under high pressure conditions and a small portion of the mobility separated sample can be transported through an interface to the MS. The collection plate can have an opening that matches the geometry of the IMS-MS interface design. The MS can be used as an online monitoring device for what is collected on the collection plate. Selective collection on this plate can be achieved by using asymmetric IMS as an ion filter, by adding a second ion gate for a symmetric IMS, or both. For example, ions with one mobility property (to the best resolution of a given device) are collected on a plate, and used for preparative, analytical purposes, or both. Furthermore, if a transverse electric field at the interface for MS is used; multiple stage ion mobility based separation can be achieved according to ions symmetric or asymmetric ion mobility properties. In various embodiments, this tandem ion mobility separation can produce high mobility separation efficiency.

Smaller pressure difference between IMS and quadrupole MS is preferred for better ion transportation efficiency. In addition, quadrupole MS is also preferred for quantitative measurements. Finally, as a practical matter, the quadrupole MS often has the lowest development and manufacturing cost compared to other MS in the current MS market. From an instrument application point of view, IMS-QMS can be a preferred choice as a fast screening tool for enantiomeric excess measurement. The optical purity is numerically equivalent to the enantiomeric excess, which is defined as: Enantiomeric excess %=[mole fraction (major enantiomer)−mole fraction (minor enantiomer)]×100.

In various embodiments, it can increase the throughput in these measurements, specifically in the initial stages of the drug discovery process where hundreds or thousands of drug compounds are being screened as potential drug candidates. In various embodiments, it can also be used as a rapid QA/QC method of pharmaceutical products. In addition, various embodiments of the chiral separation IMS-QMS of the present inventions are compatible detection methods for current preparative chiral separation methods, such as SFC and HPLC.

In various embodiments, a chiral separation IMS-MS of the present inventions can be a desktop unit that has a comparable size with current analytical HPLC systems. An integrated data acquisition system can be used to control both IMS and MS. Multiple infusion points on the drift gas inlet manifold can be implemented to allow multiple chiral modifiers to be introduced into the IMS-QMS system. In various embodiments, rapid switching among chiral modifiers with different chemical structures can reduce method development time from days to weeks for chiral chromatography to several minutes on the CIMS-QMS.

The present inventions also contemplate a stand alone Chiral Ion Mobility Separator (CIMS) system without MS. In various embodiments, CIMS can be used as a rapid and low cost chirality and enantiomeric excess detector of known samples. This configuration, e.g., can be preferred when used as a portable QA/QC equipment for pharmaceutical products. A chiral separation IMS-time of flight mass spectrometer system is one of the possible embodiments for chiral separation IMS systems; interfacing with a chromatographic system it could be a method of choice for the analysis biomarkers, metabolites or other complex biological samples while chirality of these molecules is of interests.

As already mentioned, the present invention is applicable in principle also to the separation and collection of nonchiral analyte components such as; isomers, stereoisomers, but not limited to these. If, for example, the analyte components contain a double bond (olefin) in which the first analyte components' double bond is in the cis configuration and the second analyte components' double bond is in the trans configuration, then the separating substance(s) can interact selectively to some degree with either the cis or trans configuration enhancing analyte component separation. In addition and already mentioned, the present invention is applicable to using nonchiral separating substance(s) for the separation of chiral and/or nonchiral analyte components. If, for example, the separating substance can be a particle such as helium, argon, nitrogen, carbon dioxide, but not limited to these. It has been shown that these gases used as the drift gas have differing polarizability values and do not affect all ions equally [Asbury, G. Reid; Hill Jr., Herbert H.; Anal. Chem. 2000, 72, 580-584 and Beegle, Luther W.; Kanik, Isik; Matz, Laura; Hill Jr., Herbert H.; International Journal of Mass Spectrometry 216 (2002) 257-268]. This effect can be exploited in order to alter the separation factors between different analyte components by mixing the particle (separating substance(s)) into the drift gas.

The following examples are intended to illustrate certain embodiments of the present invention, but do not exemplify the full scope of the invention.

Figure 12:
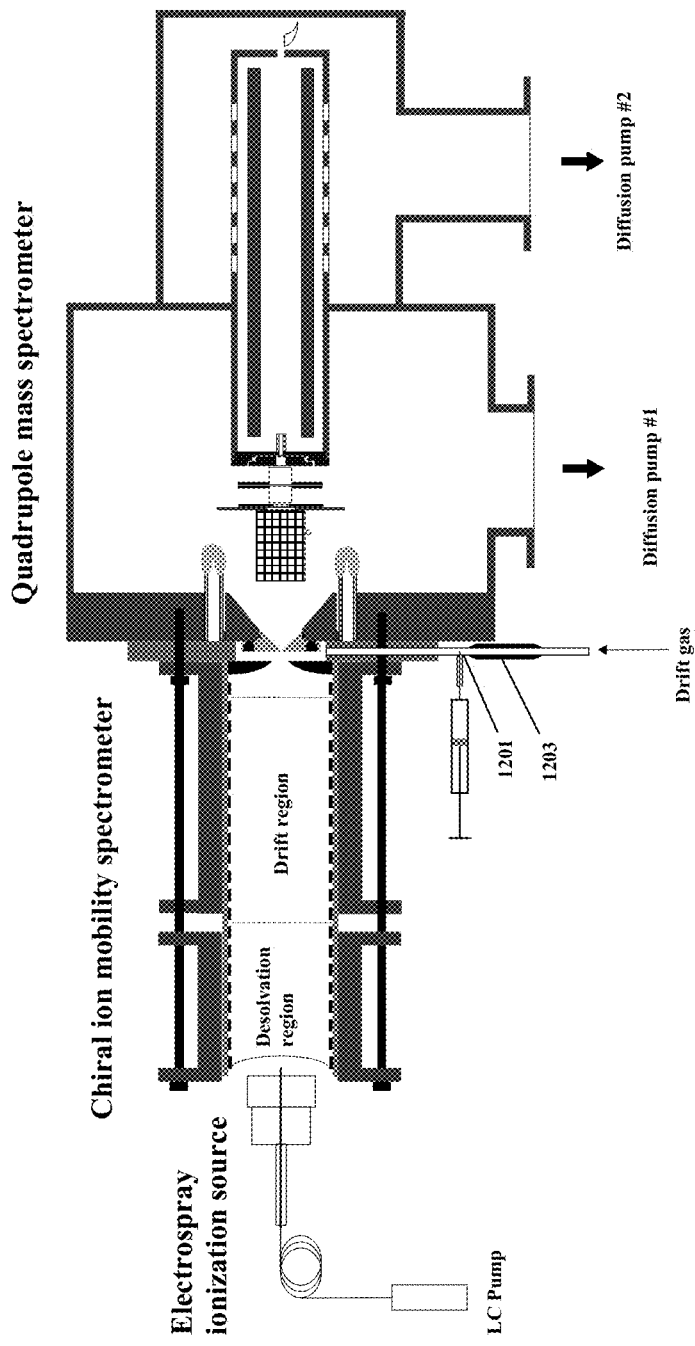
FIG. 12 shows a schematic diagram of an ESI-IMS-MS. The ion mobility spectrometer contains an electrospray ionization source; a desolvation region and an ion drift region separation by a Bradbery-Nelson ion gate; it was operated at atmospheric pressure in the examples.

The preliminary data of the following examples was obtained on an electrospray ionization-ion mobility spectrometer-quadrupole mass spectrometer (ESI-IMS-QMS) system. The system has been modified for continuous infusion of the chiral modifier into a preheated drift gas. The system is schematically shown in FIG. 12, the chiral modifier was pumped into the drift gas supply line through a "T" fitting 1201 located behind the preheating element 1203. The transfer line after the infusion point is maintained at substantially the same temperature to prevent condensation of the chiral modifier. A substantially constant chiral modifier concentration in the drift gas was maintained in the about 1 to about 20 ppm range for the experiments unless indicated otherwise. The temperature of the drift region, desolvation region and the drift gas was set at 200° C. for all experiments.

In the experiments, the analyte enantiomers were directly electrosprayed into IMS. The enantiomeric ions are formed and desolvated in the desolvation region, and separated in the drift region of the IMS. After mobility based separation, the ions were mass identified by the quadrupole mass spectrometer. In most of the experiments, the MS was operated in the single ion monitoring mode to selectively detect targeted enantiomers. Typically, the separation in the drift tube can be accomplished within 30 milliseconds and the ion identification in MS can be achieved within a few milliseconds. To achieve a desired signal to noise ratio, the spectrometer was set to signal average multiple ion mobility spectra for a few seconds in total.

EXAMPLE 1

Figure 13:
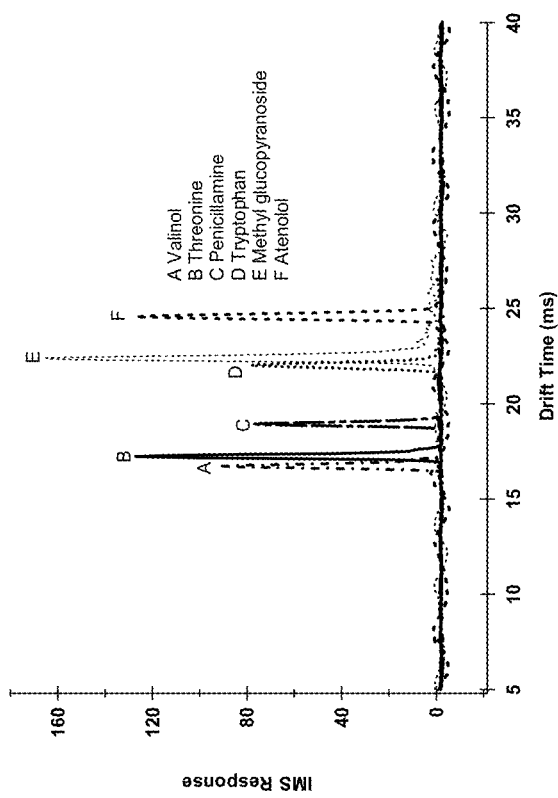
FIG. 13 shows a graph of superimposed IMS spectra of racemic mixtures of valinol, threonine, penicillamine, tryptophan, methyl-α-glucopyranoside and atenolol, where pure nitrogen was used as the drift gas. As expected, separation of the enantiomers in pure nitrogen drift gas was not achieved.

FIG. 13 shows superimposed ion mobility spectra of racemic mixtures in a pure nitrogen drift gas (no chiral modifier added). Each enantiomer in the electrospray solution was at a concentration of 100 ppm. Samples were introduced into the IMS via the electrosprayer with a flow rate of 1 μL/min. The enantiomeric mixtures showed in FIG. 13 are D- and L-valinol, D and L-threonine, D- and L-penicillamine, D and L-tryptophan, D- and L-methyl-α-glucopyranoside and R- and S-atenolol. These spectra represent data that can be obtained using a conventional ion mobility spectrometer. Even though these test enantiomeric mixtures could be separated from each other in the IMS, no enantiomeric separation was observed for the racemates in nitrogen drift gas without chiral modifier.

EXAMPLE 2

Figure 14:
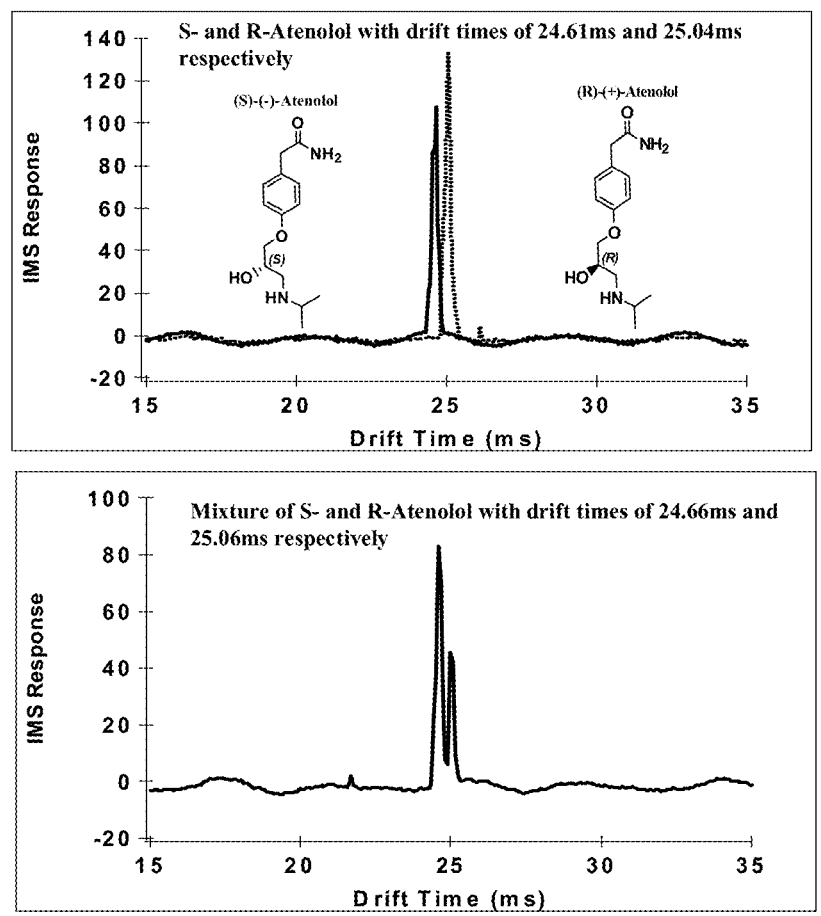
FIG. 14 shows two graphs of the gas phase separation of atenolol enantiomers. The upper graph shows the superimposed spectra of S- and R-atenolol obtained after introduction of S-(+)-2-butanol as the chiral modifier in the drift gas. The bottom graph demonstrates the IMS separation of an enantiomeric mixture of S- and R-atenolol.

Atenolol is from a class of drugs called beta-blockers mainly prescribed alone or in combination with other medications to treat high blood pressure and lower heart rate, to prevent angina and to reduce the risk of recurrent heart attacks. Chiral Ion Mobility Separator (CIMS) separation of S- and R-atenolol enantiomeric mixture is illustrated in FIG. 14. When no chiral modifier was introduced to the drift gas, drift times for the S- and R-enantiomers were almost identical at 24.56 and 24.51 ms, respectively. In the CIMS, The drift times of S- and R-atenolol were 24.61 ms and 25.04 ms respectively when analyzed individually; the drift times of S- and R-atenolol were 24.66 ms and 25.06 ms when analyzed as a mixture. It was observed that drift time shift of R-atenolol was more significant compared to S-atenolol.

EXAMPLE 3

Figure 15:
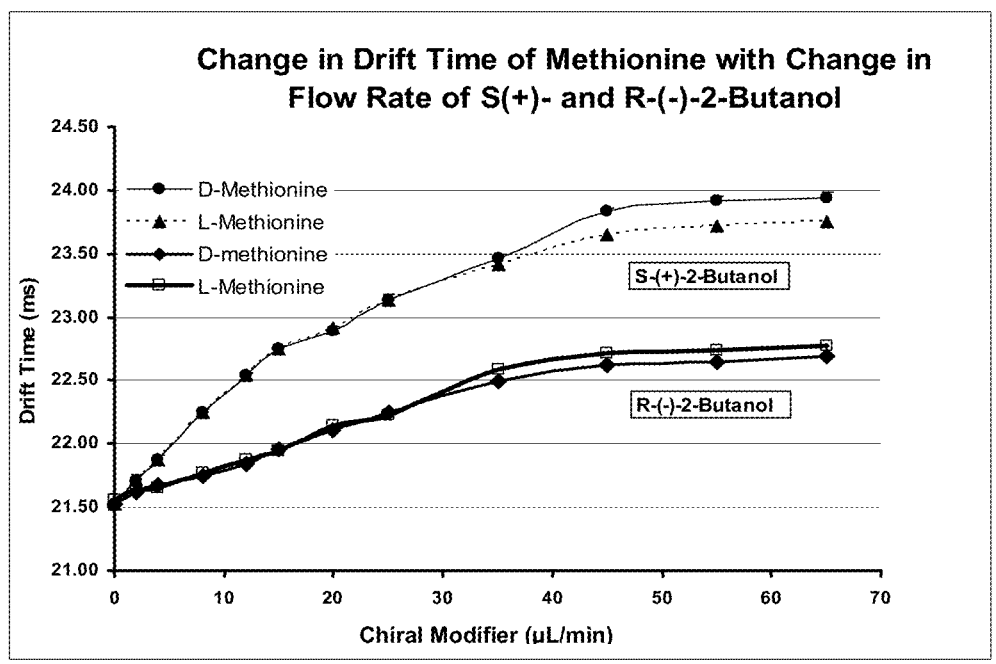
FIG. 15 shows a graph showing the effects of chirality and flow rate of the chiral modifier on the drift times of the methionine enantiomers in CIMS. A better separation of methionine enantiomers was observed with S-(+)-2-butanol compared to R-(−)-2-butanol. The order of elution was reversed when the chirality of the modifier was reversed. Preferred chiral modifier flow rate was at ~45 µL/min corresponding to 10 ppm in the drift gas.

To illustrate how a chiral modifier affects separation in a CIMS, the drift times of individual enantiomers, L- and D-methionine, were recorded as a function of infusion flow rate of the chiral modifiers introduced into the drift gas. In the experiments, μL/min of a liquid chiral modifier, S-(+)-2-butanol or R-(−)-2-butanol, was pumped into and volatilized in the preheated nitrogen gas stream. The results of this investigation are shown in FIG. 15.

The drift times of methionine enantiomers increased with the introduction of chiral modifier, S-(+) or R-(−)-2-butanol. When S-(+)-2-butanol was used as the chiral modifier the drift time of both enantiomers, D- and L-methionine increased as a function of the concentration of the chiral modifier in the nitrogen drift gas. However, no difference in the drift time of the enantiomers could be seen until the chiral modifier flow rate reached about 30 μL/min. With only nitrogen as the drift gas, the drift time of both methionine enantiomers was 21.52±0.04 ms. With a chiral modifier flow rate at 5 μl/min, the drift time of methionine enantiomers shifted to 22.12 ms. At a chiral modifier flow rate of 45 µl/min, the drift times were 23.83±0.03 ms for D-methionine and 23.64±0.04 ms for L-methionine. A 0.8% change in the separation factor between the enantiomers was observed, where the separation factor is defined as the ratio of the $t_2/t_1$; $t_1$ and $t_2$ are drift time of the two enantiomers.

With a chiral modifier flow rate below about 30 µl/h, both L- and D-methionine drift time increased with the gas phase concentration of chiral modifiers. The drift time increase was caused, it is believed without being held to theory, by drift gas composition change, which reflects changes of ion-molecular interaction in the CIMS. However, it is believed that this interaction is not related to molecular chirality. When chiral modifier concentrations reached a certain level, the selective interaction between enantiomers and chiral modifiers could be observed. The drift time shifts started to show differences according to their chiralities. Significant change in separation factor was observed beyond the flow rate of about 45 µl/h of S-(+)-2-butanol. The flow rate of 45 µl/min of S-(+)-2-butanol corresponds to a mixing ratio of approximately 10 ppm of S-(+)-2-butanol in nitrogen at standard temperature and pressure.

A smaller shift in drift time was observed with R-(−)-2-butanol as the chiral modifier. The maximum shift in separation factor was about 0.4% between the enantiomers. However, with R-(−)-2-butanol, L-methionine drifted longer than D-methionine. The enantiomers were identified by measuring the drift time of each enantiomer separately under substantially identical experimental conditions. Based on this data, S-(+)-2-butanol was chosen as the chiral modifier at a flow rate of 45 µL/min for the remainder of these experiments.

Figure 16:
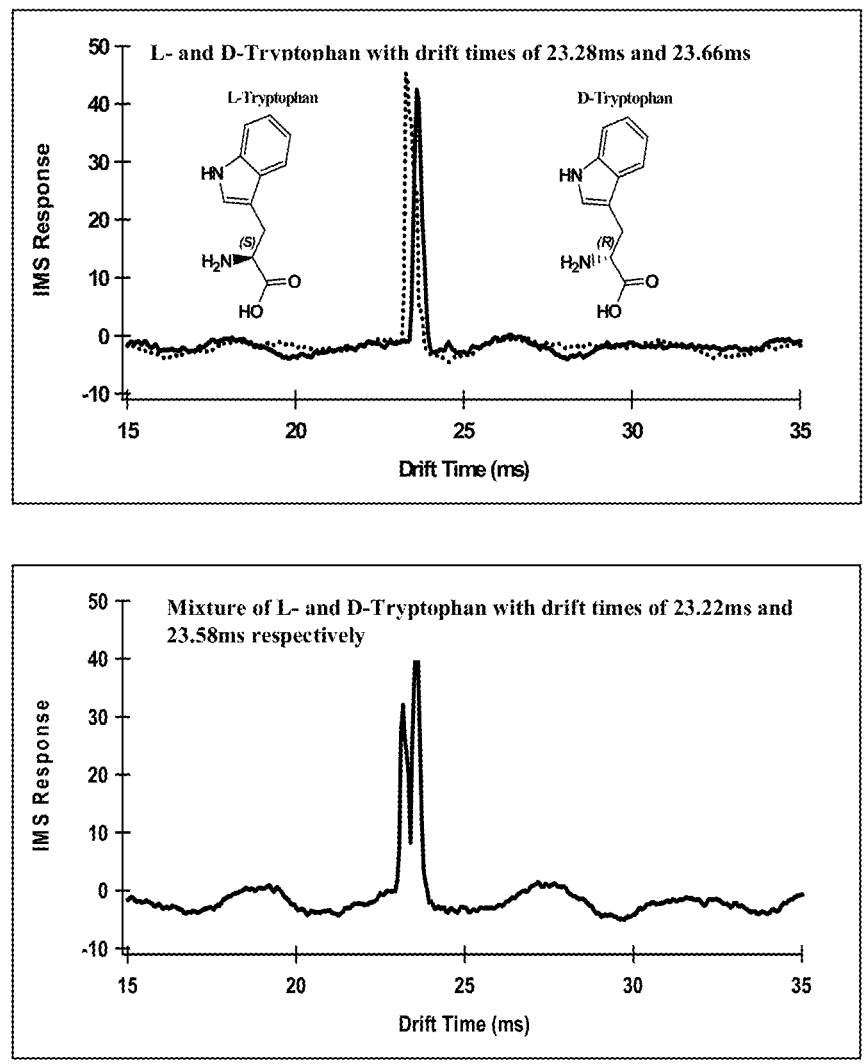
FIG. 16 shows two graphs of the CIMS-MS separation of L- and D-tryptophan. The upper graph shows the superimposed spectra of L- and D-tryptophan obtained independently. The bottom graph demonstrates the separation of the enantiomeric mixture of L- and D-tryptophan.

Similarly, tryptophan enantiomers were used to demonstrate CIMS separation under substantially the same experiment conditions. FIG. 16 illustrates the gas phase separation of tryptophan enantiomers when S-(+)-2-butanol was used as the chiral modifier in the drift gas. The upper graph of FIG. 16 shows the drift times of L- and D-Tryptophan are 23.28 ms and 23.66 ms, respectively, when analyzed individually. The bottom graph shows the separation of the enantiomers from a mixture of L- and D-Tryptophan. The measured drift times of L- and D-Tryptophan were 23.22 ms and 23.58 ms, respectively, when measured as mixture. With no chiral modifier in the gas, drift times of L- and D-Tryptophan were nearly identical, 22.02 ms and 21.99 ms respectively. In this case, both enantiomers interacted significantly with the chiral modifier but the interaction between D-Tryptophan and S-(+)-2-butano was stronger than L-Tryptophan, thus the separation of L- and D-Tryptophan became possible.

EXAMPLE 4

Figure 17:
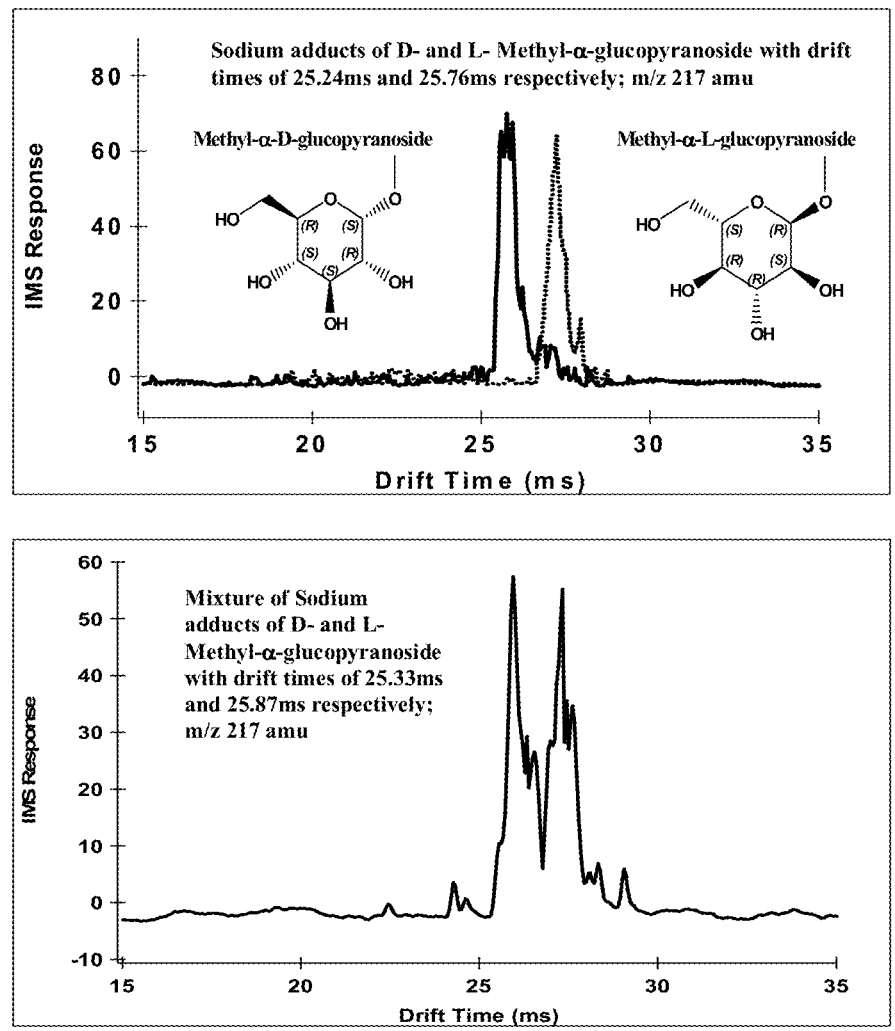
FIG. 17 shows two graphs of CIMS-MS separation of L- and D- and Methyl-α-glucopyranoside Ion mobility spectra of sodium adduct of D- and L-Methyl-α-glucopyranoside enantiomers. The upper graph shows the superimposed spectrum of D- and L-Methyl-α-glucopyranoside enantiomers obtained independently. The bottom graph demonstrates the separation of the enantiomeric mixture of D- and L-Methyl-α-glucopyranoside.

FIG. 17 shows CIMS separation of the sodium adducts of D- and L-Methyl-α-glucopyranoside. The difference in drift time shifts of D- and L-Methyl-α-glucopyranoside were significant. Strong chiral selective interaction of the S-(+)-2-butanol and Methyl-α-glucopyranoside enantiomers was observed. It is believed, without being held to theory, that the stronger interaction was the result of multiple-point selective interaction between the chiral modifier and Methyl-α-glucopyranoside enantiomers with multiple chiral centers.

EXAMPLE 5

Figure 18:
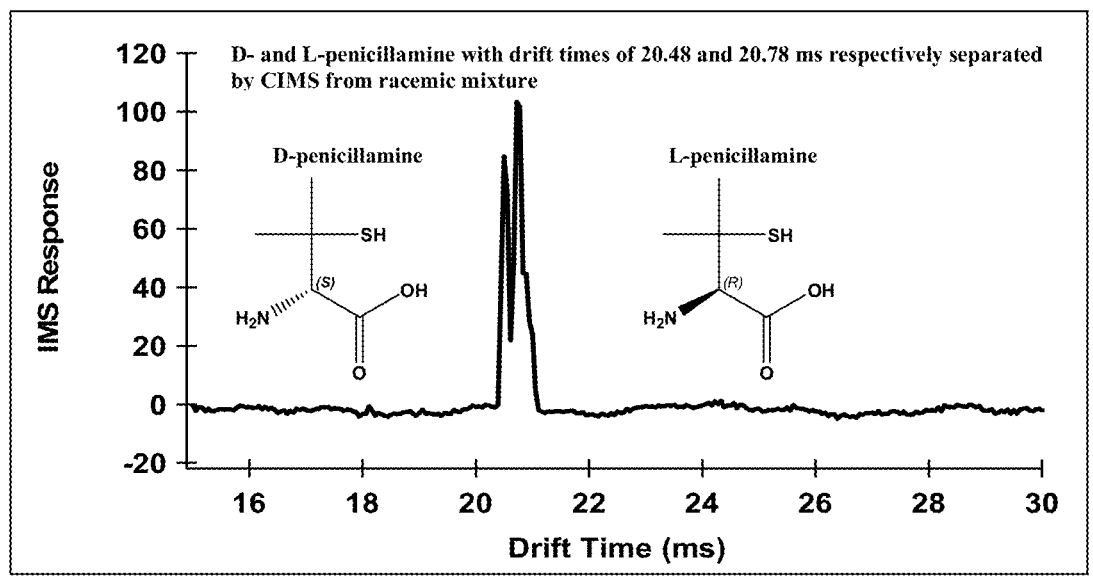
FIG. 18 shows the graph of an IMS separation of the enantiomeric mixture L- and D-penicillamine.

FIG. 18 shows CIMS separation of the D- and L-penicillamine. Without aromatic rings in the penicillamine structure, the observed drift time difference between D- and L-penicillamine was relatively small.

Table 1 Summarizes the results of most of the enantiomers studied in these examples. It shows a comparison of the drift times and mobilities of enantiomers with and without chiral modifier infused in the drift gas. The first column lists measured m/z of identified enantiomeric ions; the second column identifies the test compounds; the third column shows their drift times in pure nitrogen; the fourth column shows their drift times with the presence of chiral modifier, S-(+)-2-butanol; the fifth and sixth columns show calculated reduced mobility values according to measured drift time. The data demonstrates that when chiral modifier is added to the drift gas, the drift time of both enantiomers are elongated, however, one enantiomer always has a greater shift compared to the other due to structure selective interaction between chiral modifier and the enantiomers.

Using S-(+)-2-butanol as the chiral modifier at a infusion flow rate of 45 µL/min, Table 1 reports the drift times and mobilities of a variety of enantiomers. When the drift gas was mixed with chiral modifier, the drift times of enantiomers were no longer the same. A 2-28% shift in the drift times of the analyzed samples was observed when the chiral modifier was added to the nitrogen drift gas. Compared to the drift time in pure nitrogen, the maximum observed drift time difference was about 5.2 ms for methionine when S-(+)-2-butanol was introduced. This suggests that methionine had the strongest interaction with the chiral modifier as compared to other analyzed samples. The minimum shift was observed for atenolol, which was about 0.6 ms. It was observed that even though methionine experienced interaction in chirally modified drift gas, the difference in the drift times of the enantiomeric ions was the least among the samples studied. The maximum difference in the drift times between the enantiomeric pair was observed between D- and L-methyl-α-glucopyranoside and D- and L-serine of the samples studied. On average, a 2% deviation in drift times between the enantiomers was observed in IMS.

It is believed, without being held to theory, that the above observations indicate that the interaction between chiral modifier and targeted enantiomers can be divided into two categories, chiral selective or non-chiral selective interactions. The drift time shift caused by non-chiral selective interaction may include enhanced elastic collision or other long-range gas phase interactions between the modifier and analyte ions. Even though the interaction force can be strong, the drift time of enantiomers shifted at the same degree because the enantiomers had identical or substantially identical properties involved in the interactions. CIMS relies on the chiral selective interaction that involves, it is believed, the functional group(s) around a chiral center of the enantiomers. Multiple chiral centers in D- and L-methyl-α-glucopyranoside seem to enhance the chiral selective interaction significantly.

The gas phase separation of each enantiomeric pair was repeated for a statistically significant number of times to determine reproducibility. Overall the reproducibility of the drift times was excellent and similar to that achieved when no chiral modifier was introduced. The standard deviations of the measurements ranged from 0.03 to 0.05 ms. Thus, the drift time and ion mobilities were measured reproducibly within a RSD of 0.2%.

The present examples indicate that the parameters that tend to have the most impact on governing the performance of the ion mobility separator for chiral compounds are separator temperature and chiral modifier concentration. In the present examples, methionine was used to explore required chiral modifier concentration to separate enantiomeric ions.

It was observed in common ion mobility experiments that ion-molecular interaction was more significant when the spectrometer is operated under lower temperature (<100° C.) as opposed to higher temperatures. Most of the data was obtained at under 200° C. conditions.

Biologically active molecules can also be separated by CIMS. A few selected examples of biologically active molecules suitable for testing of and evaluating CIMS-MS performance include, but are not limited to, those in Table 2. This group of chiral analytes can be prepared in a solution that can be electrosprayed into CIMS. The solutions may contain single enantiomers or mixtures with known enantiomeric ratio. These samples can be used, e.g., for system optimization, chiral modifier selection, performance comparison with other separation methods, etc.

In general, IMS is referred as a semi-quantitative method. Quantitative measurement capability of IMS is limited by the ionization process as charge transfer reactions are commonly used to ionize target molecules. The charge competition process in electrospray ionization source, for example, can prevent target molecule from being completely ionized in a mixture. As a result the measured peak height cannot be quantitatively related back to liquid phase concentration when charge competition processes exist. However, for the purpose of chiral separation and detection, the charge competition will not affect the measured enantiomeric excess because the enantiomers have identical or substantially identical charge affinity and should have an equal or a substantially equal probability of being ionized. As one set of practical tests, common chiral drugs, such as atorvastatin, clopidogrel, olanzapine, etc., can be prepared in suitable electrospray solvents, and then introduced to an IMS system for the assessment of enantiomeric excess.

The data acquired was analyzed to seek information and develop a fuller understanding of the relationship between drift time shift and chirality. Some indication has been found in the data that the drift time shift of L- and D-Methionine was reversed when the chirality of the modifier is reversed.

The elution order of the chiral molecules from the CIMS is determined by running a single enantiomer standard. However, the chiral modifiers in CIMS can be easily switched from one chirality to another within seconds. If the chirality is predicted with the information obtained using multiple chiral modifier with multiple chirality, the same result will be obtained much faster than testing single enantiomer standards separately.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

While the inventions have been particularly shown and described with reference to specific illustrative embodiments, it should be understood that various changes in form and detail may be made without departing from the spirit and scope of the inventions. By way of example, any of the disclosed ionization sources, ion mobility separators and ion collectors can be combined in any combination to provide an apparatus for the separation of chiral molecules in accordance with various embodiments of the invention. Therefore, all embodiments that come within the scope and spirit of the inventions, and equivalents thereto, are claimed. The descriptions and diagrams of the methods, systems, and assays of the present inventions should not be read as limited to the described order of elements unless stated to that effect.

TABLE 1

| IONS (M/Z) | TEST COMPOUNDS | CHIRALITY AND TD, OF ENANTIOMERS IN N2 | | CHIRALITY OF ENANTIOMERS AND $T_D$ WITH S-(+)-2-BUTANOL | | KO ENANTIOMERS IN N2 | | KO OF ENANTIOMERS IN S-(+)-2-BUTANOL | |
|---|---|---|---|---|---|---|---|---|---|
| 267 (M + H)+ | R AND S- ATENOLOL | (S), 24.56 ± 0.03 | (R), 24.51 ± 0.03 | (S), 24.66 ± 0.04 | (R), 25.06 ± 0.05 | 1.18 | 1.18 | 1.18 | 1.16 |
| 205 (M + H)+ | D AND L- TRYPTOPHAN | (D), 22.02 ± 0.03 | (L), 21.99 ± 0.04 | (D), 23.22 ± 0.05 | (L), 23.63 ± 0.05 | 1.32 | 1.32 | 1.25 | 1.23 |
| 150 (M + H)+ | D AND L- METHIONINE | (D), 18.61 ± 0.04 | (L), 18.66 ± 0.04 | (D), 23.59 ± 0.04 | (L), 23.83 ± 0.06 | 1.56 | 1.56 | 1.23 | 1.22 |
| 120 (M + H)+ | D AND L- THREONINE | (D), 17.22 ± 0.03 | (L), 17.20 ± 0.04 | (D), 19.22 ± 0.05 | (L), 19.61 ± 0.05 | 1.69 | 1.69 | 1.51 | 1.48 |
| 217 (M + NA)+ | D- AND L- METHYL-A-GLUCOPYRANOSIDE | (D), 22.42 ± 0.05 | (L), 22.40 ± 0.05 | (D), 25.33 ± 0.08 | (L), 25.87 ± 0.07 | 1.30 | 1.30 | 1.15 | 1.12 |
| 203 (M + NA)+ | D- AND L- METHYL-A-GLUCOSE | (D), 22.35 ± 0.04 | (L), 22.32 ± 0.03 | (D), 23.61 ± 0.05 | (L), 23.98 ± 0.04 | 1.30 | 1.30 | 1.23 | 1.21 |
| 150 (M + H)+ | D- AND L- PENICILLAMINE | (D), 18.94 ± 0.03 | (L), 18.92 ± 0.05 | (D), 20.48 ± 0.03 | (L), 20.78 ± 0.04 | 1.53 | 1.53 | 1.42 | 1.40 |
| 104 (M + H)+ | D AND L- VALINOL | (L), 16.72 ± 0.04 | (D), 16.75 ± 0.03 | (L), 17.84 ± 0.04 | (D), 18.26 ± 0.04 | 1.74 | 1.74 | 1.62 | 1.60 |
| 166 (M + H)+ | D AND L- PHENYLALANINE | (L), 20.07 ± 0.04 | (D), 20.05 ± 0.04 | (D), 22.22 ± 0.03 | (L), 22.61 ± 0.05 | 1.45 | 1.45 | 1.31 | 1.28 |
| 106 (M + H)+ | D AND L- SERINE | (D), 16.82 ± 0.03 | (L), 16.83 ± 0.04 | (D), 18.72 ± 0.04 | (L), 19.11 ± 0.05 | 1.73 | 1.73 | 1.55 | 1.52 |

TABLE 2

| NUCLEOTIDE | AMINO ACID/PEPTIDE | ALKALOID PSEUDO-EPHEDRINE |
|---|---|---|
| 8-OXO-2' DEOXY GUANOSINE 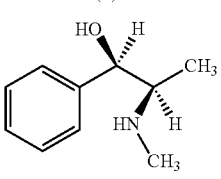 | N,N-DIBENZYL-D-SERINE METHYL ESTER 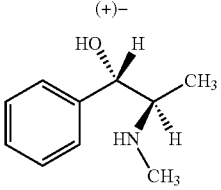<br><br>N,N-DIBENZYL-L-SERINE METHYL ESTER 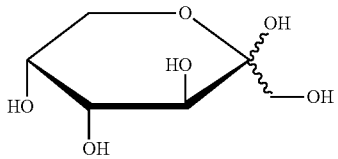 | (−)− 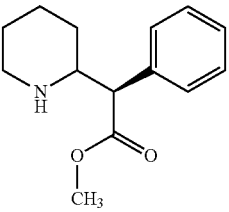<br><br>(+)− |
| CARBOHYDRATE FRUCTOSE | DRUG THREO-METHYLPHENIDATE | CARCINOGEN N'-NITROSONORNICOTINE |
| (D)- 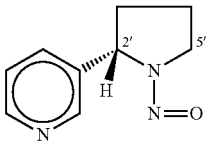<br><br>(L)- | (D)- 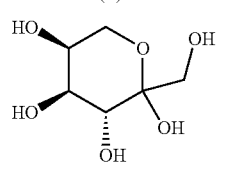<br><br>(L)- | (S)- 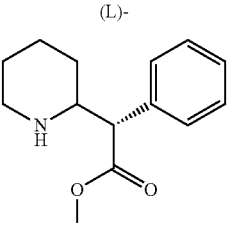<br><br>(R)- 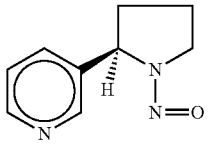 |

What is claimed is:

1. An apparatus for the ionization of a sample comprising:
   (a) at least one primary electrospray ionization source that substantially ionizes at least one portion of the sample into gas phase ions;
   (b) at least one secondary electrospray ionization source that is spatially separated from the primary electrospray ionization source, and which ionizes an un-ionized portion of the same sample into gas phase ions;
   (c) a ionization chamber containing an independent electric field having a first direction along a longitudinal axis of the ionization chamber that guides charged particles in the ionization chamber along the axis
   (d) a gas flow that is confined by the ionization chamber transporting the portion of the sample that is not ionized by the primary electrospray ionization source along a second direction to separate that portion from the ionized portion, where the angle between the first and second directions is substantially greater than zero; and
   (e) at least one analyzer in fluid communication with the ionization chamber for the analysis of all ionized portions of the sample.

2. The apparatus of claim 1, wherein the analyzer is an ion mobility separator or a mass analyzer.

3. The apparatus of claim 2, wherein the mass analyzer is a quadrupole, an ion trap, or a time of flight mass analyzer.

4. The apparatus of claim 1, wherein the analyzer is interfaced to the ionization chamber between substantially zero and substantially one hundred eighty degrees from the direction of the electric field.

5. The apparatus of claim 1, wherein the secondary electrospray ionization source further comprises chemical modifiers.

6. A method for the ionization of samples comprising the steps of:
   (a) introducing a sample into a ionization chamber that has an independent electric field along a first axis with a first direction, where said independent electric field is independent from that generated by the ion source;
   (b) ionizing a portion of the sample by a primary electrospray ionization source;
   (c) guiding the ionized portion of the sample using the independent electric field along the first direction;
   (d) carrying the un-ionized portion of the same sample using a gas flow along a second axis with a second direction; where the angle between the first and second axis is substantially greater than zero;
   (e) ionizing a portion of the un-ionized sample by a secondary electrospray ionization source that is spatially separated from the primary electrospray ionization source; and
   (f) extracting the ionized sample from the ionization chamber into an analyzer for the analysis of all ionized portions of the sample.

7. The method of claim 6, wherein the step of ionizing further comprises introducing a chemical modifiers into the ionization source.

8. The method of claim 6, wherein the step of introducing the sample comprises a continuous or pulsed sample flow.

9. The method of claim 6, wherein the step of ionizing the un-ionized portion of the sample comprises bringing charged particles generated by the secondary electrospray ionization source into the ionization chamber continuously or as pulses.

10. The method of claim 6, wherein the steps of (c) (d) and (e) are repeated.

* * * * *